US008357893B2

(12) United States Patent
Xu et al.

(10) Patent No.: US 8,357,893 B2
(45) Date of Patent: Jan. 22, 2013

(54) ION MOBILITY SENSOR SYSTEM

(75) Inventors: Jun Xu, Knoxville, TN (US); David B. Watson, Knoxville, TN (US); William B. Whitten, Oak Ridge, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 272 days.

(21) Appl. No.: 12/586,619

(22) Filed: Sep. 23, 2009

(65) Prior Publication Data
US 2011/0068264 A1    Mar. 24, 2011

(51) Int. Cl.
*H01J 49/00* (2006.01)
(52) U.S. Cl. ........ 250/290; 250/281; 250/288; 250/294; 250/296; 250/423 R; 250/423 F; 250/287
(58) Field of Classification Search .......... 250/281, 250/288, 294, 296, 423 R, 423 F, 290
See application file for complete search history.

(56) References Cited

U.S. PATENT DOCUMENTS

| | | | |
|---|---|---|---|
| 5,010,776 A * | 4/1991 | Lucero et al. | 73/863.23 |
| 5,110,473 A * | 5/1992 | Hassett | 210/634 |
| 5,626,758 A * | 5/1997 | Belfort | 210/636 |
| 6,635,871 B2 | 10/2003 | Xu et al. | |
| 6,822,225 B2 | 11/2004 | Xu et al. | |
| 7,119,328 B2 | 10/2006 | Kaufman et al. | |
| 7,179,636 B2 * | 2/2007 | Guillot et al. | 435/261 |
| 7,199,362 B2 | 4/2007 | Rockwood et al. | |
| 2004/0004040 A1 | 1/2004 | Colling et al. | |
| 2006/0226353 A1 * | 10/2006 | Tang et al. | 250/287 |
| 2006/0289809 A1 | 12/2006 | Bonne et al. | |
| 2007/0176092 A1 | 8/2007 | Miller et al. | |
| 2008/0135497 A1 | 6/2008 | Fuchs et al. | |
| 2009/0224150 A1 * | 9/2009 | Matyjaszczyk et al. | 250/282 |

FOREIGN PATENT DOCUMENTS

WO    WO2007/086831    *    8/2007    ............ 250/290

(Continued)

OTHER PUBLICATIONS

International Search Report and Written Opinion of the International Searching Authority for PCT/US2010/049798, Aug. 2, 2007, pp. 11.

(Continued)

*Primary Examiner* — Jack Berman
*Assistant Examiner* — Meenakshi Sahu
(74) *Attorney, Agent, or Firm* — Brinks Hofer Gilson & Lione

(57) ABSTRACT

An ion mobility sensor system including an ion mobility spectrometer and a differential mobility spectrometer coupled to the ion mobility spectrometer. The ion mobility spectrometer has a first chamber having first end and a second end extending along a first direction, and a first electrode system that generates a constant electric field parallel to the first direction. The differential mobility spectrometer includes a second chamber having a third end and a fourth end configured such that a fluid may flow in a second direction from the third end to the fourth end, and a second electrode system that generates an asymmetric electric field within an interior of the second chamber. Additionally, the ion mobility spectrometer and the differential mobility spectrometer form an interface region. Also, the first end and the third end are positioned facing one another so that the constant electric field enters the third end and overlaps the fluid flowing in the second direction.

23 Claims, 14 Drawing Sheets

FOREIGN PATENT DOCUMENTS

WO     WO 2007/086831 A2     8/2007

OTHER PUBLICATIONS

Search History for PCT/US2010/049798, Jan. 19, 2011, pp. 4.

M. LaPack et al., *Membrane mass spectrometry for the direct trace analysis of volatile organic compounds in air and water*, Anal. Chem. 1990, vol. 62, No. 13, pp. 1285-1271, Jul. 1, 1990.

I.A. Buryakov, *A new method of separation of multi-atomic ions by mobility at atmospheric pressuring using a high-frequency amplitude-asymmetric strong electric field*, International Journal of Mass Spectrometry and Ion Processes, vol. 128, pp. 143-148, 1993.

T. Kotiaho et al., *Membrane inlet ion mobility spectrometer for on-line measurement of ethanol in beer and in yeast fermentation*, Analytica Chimica Acta, vol. 309, pp. 317-325, 1995.

G. Simpson et al., *Evaluation of Gas Chromatography Coupled with Ion Mobility Spectrometry for Monitoring Vinyl Chloride and Other Chlorinated and Aromatic Compounds in Air Samples*, J. High Resol. Chromatogr., vol. 19, Issue 6, pp. 301-312, Jun. 1996.

A. Donò et al., *Abatement of Volatile Organic Compounds by Corona Discharge. A study of the Reactivity of Trichloroethylene Under Atmospheric Pressure Ionization Conditions*, Rapid Commun. Mass Spectrom., 1997, vol. 11, pp. 1687-1694.

R. Guevremont et al., *Atmospheric pressure ion focusing in a high-field asymmetric waveform ion mobility spectrometer*, Rev. Sci. Instrum., vol. 70, No. 2, pp. 1370-1383, Feb. 1999.

C. Lock et al., *Simulation of Ion Trajectories through a High Pressure Radio Frequency Only Quadrupole Collision Cell by SIMION 6.0*, Rapid Commun. Mass Spectrom., 1999, vol. 13, pp. 422-431.

S. Sielemann et al., *Detection of trans-1,2-dichloroethene, trichloroethene and tetrachloroethene using Multi-Capillary Columns Coupled to Ion Mobility Spectrometer with UV-Ionisation Sources*, International Journal for Ion Mobility Spectrometry, vol. 2, No. 1, pp. 15-21, 1999.

R. A. Miller et al., *A novel micromachined high-field asymmetric waveform-ion mobility spectrometer*, Sensors and Actuators B: Chemical, vol. 67, Issue 3, pp. 300-306, Sep. 1, 2000.

J. Xu et. al., *Space Charge Effects on Resolution in a Miniature Ion Mobility Spectrometer*, Anal. Chem. 2000, vol. 72, No. 23, pp. 5787-5791, Dec. 1, 2000.

A Nicoletti et al., *Ion chemistry of chloroethanes in air at atmospheric pressure*, Rapid Commun. Mass Spectrom. 2001, vol. 15, pp. 1904-1911.

J. Stach et al., *A Simple Field Method for Determination of MTBE in Water Using Hand Held Ion Mobility (IMS)*, International Journal for Ion Mobility Spectrometry, vol. 5, No. 3, pp. 82-86, 2002.

J.W. Leonhardt, *A new ppb-gas analyzer by means of GC-ion mobility spectrometry (GC-IMS)*, Journal of Radioanalytical and Nuclear Chemistry, vol. 257, No. 1, pp. 133-139, Kluwer Academic Publishers, Dordrecht, 2003.

J. Xu et. al., *Pulsed-Ionization Miniature Ion Mobility Spectrometer*, Anal. Chem. 2003, vol. 75, No. 16, pp. 4206-4210, Aug. 15, 2003.

G. A. Eiceman et al., *Differential mobility spectrometry of chlorocarbons with a micro-fabricated drift tube*, The Analyst, 2004, vol. 129, No. 4, pp. 297-304, Feb. 20, 2004.

D. B. Watson et al., *Plume and Lithologic Profiling with Surface Resistivity and Seismic Tomography*, Ground Water, vol. 43, No. 2, pp. 169-177, Mar.-Apr. 2005.

G. Walendzik et al., *Coupling of SPME with MCC/UV-IMS as a tool for rapid on-site detection of groundwater and surface water contamination*, Anal. Bioanal. Chem. vol. 382, pp. 1842-1847, Jul. 30, 2005.

R. T. Short et al., *Detection and quantification of chemical plumes using a portable underwater membrane introduction mass spectrometer*, Trends in Analytical Chemistry, vol. 25, No. 7, 2006.

P. Peeraprasompong et al., *Development of an In-Line System for the Analysis of 4,4'-DDT in Water*, Journal of Environmental Science and Health Part B, vol. 41, pp. 807-819, 2006.

J. Xu, *Micro Ion Mobility Sensor for in Situ Monitoring of Contaminated Groundwater*, SERDP, 2008.

J. Xu et al., *Sampling and Detection of Chlorinated Hydrocarbons in Water unsing Membrane-Coupled IMS*, ISIMS2009, Thun, Switerzland, Jul. 27, 2009.

\* cited by examiner

ION MOBILITY SENSOR SYSTEM

This invention was made with government support under Contract No. DE-AC05-00OR22725 awarded by the U.S. Department of Energy. The government has certain rights in the invention.

BACKGROUND OF THE INVENTION

1. Field of the Invention

The present invention relates generally to ion mobility sensor systems. Specifically, one aspect of the present invention relates to an extraction sampler and an ion mobility sensor system that uses such an extraction sampler. A second aspect of the present invention relates to an ion mobility sensor system that includes an interface which can be applied between ion mobility spectrometry (IMS) and differential mobility spectrometry (DMS) technology.

2. Discussion of Related Art

Contaminated groundwater and its associated vapor are a major concern due to the persistence of certain pollutants such as dense non-aqueous phase liquids (DNAPLs). Chlorinated hydrocarbons constitute the major portion of DNAPLs and, as such, must be monitored closely. Long-term monitoring (LTM) of these pollutants is needed not only because of their potential hazard, but also due to the reality that complete cleanup of significant DNAPL source zones has not been, and most likely will not be, possible.

Current state-of-the-art technologies for analysis of water contaminants include portable gas chromatography (GC), optical fiber, and membrane mass spectrometry (MS). Most LTM approaches usually involve the installation and maintenance of monitoring wells, labor intensive sampling, and costly laboratory analysis. These technologies are complex, large, time-consuming, require substantial utilities (power and vacuum), and have high associated costs.

For example, in performing membrane mass spectrometry, a hollow membrane is used, such that the outside surface of the membrane is in contact with a sampling substance and the internal chamber of the hollow membrane is connected to a vacuum (often called a "flow-over"). The hollow membrane is used as an inlet for providing sample gases to a mass spectrometer, which then performs mass spectrometry. This "flow-over," however, is difficult to implement due to conflicting requirements related to the use of a carrier gas. For example, if a carrier gas is used inside this hollow membrane, it can dilute the sample concentration due to the effect of the vacuum in the mass spectrometer. However, if no carrier gas is used the slow diffusion of chemicals from the sample substance along the length of the hollow membrane reduces the gradient of permeate concentrations across the membrane wall and consequently reduces permeability.

The advantages of using IMS technology are numerous, and include high sensitivity, fast response, and low cost. High sensitivity can be attributed to high electron and proton affinities of certain chemicals, as well as larger available sample sizes resulting from configurations which allow for operation in atmospheric pressure.

For example, contra-band drugs have high proton affinities and explosives have high electron affinities. Some chemicals, such as chemical warfare agents and chlorinated hydrocarbons, have both high electron affinities and proton affinities. When these chemicals enter an ionization region of an IMS spectrometer, they will preferentially obtain charge from reactant ions, forming their own characteristic ions in both negative and positive polarities, leading to high sensitivity for IMS technology. Fast response comes from the fact that ions drifting in an IMS drift cell are driven by a constant external field, which results in a fast response time, typically 5-50 milliseconds.

Another intriguing feature is that IMS is generally operated in ambient atmospheric pressure, thus alleviating the problems associated with the vacuum pressurization described with mass spectrometry. Such a feature generates many advantages, including allowing for the use of carrier gases in sampling and separation, as well as providing reliability in robust environments and inexpensive operation compared with mass spectrometry and GC.

However, certain debilitating limits also exist for such IMS spectrometers. Poor resolution is one of them, resulting in cross-sensing and false alarms. Mixture of analytes and complexity of drifting air can also mislead both identification and quantification of analytes.

Despite these limits, IMS technology has been used in many common analytical detection applications. Presently, a large number of IMS sensors are used by the US Army for detecting trace chemical warfare agents. Additionally, more than 10,000 explosive trace detectors, mostly using IMS, have been deployed by the Transportation Security Agency in U.S. airports for the interrogation of carry-on baggage. Many IMS-based detectors are being used for these and other homeland security applications, such as trace detection of drugs and other contra-band.

Although IMS technology has been used for detection of explosives, chemical warfare agents, and other contraband, current handheld IMS systems cannot be used for monitoring chlorinated hydrocarbons in groundwater due to limited resolution. Similarly, a stand-alone differential ion mobility spectrometry (DMS) spectrometer cannot adequately monitor chlorinated hydrocarbons because ions generated from unknown chemicals in groundwater alter the positions and intensities of chlorinated hydrocarbon ion peaks. A combination of an IMS spectrometer and a DMS spectrometer can achieve feasible monitoring of chlorinated hydrocarbons.

OBJECTS AND SUMMARY OF THE INVENTION

One aspect of the present invention regards an ion mobility sensor system including an ion mobility spectrometer and a differential mobility spectrometer coupled to the ion mobility spectrometer. The ion mobility spectrometer has a first chamber having first end and a second end extending along a first direction, and a first electrode system that generates a constant electric field parallel to the first direction. The differential mobility spectrometer includes a second chamber having a third end and a fourth end configured such that a fluid may flow in a second direction from the third end to the fourth end, and a second electrode system that generates an asymmetric electric field within an interior of the second chamber. Additionally, the ion mobility spectrometer and the differential mobility spectrometer form an interface region. Also, the first end and the third end are positioned facing one another so that the constant electric field enters the third end and overlaps the fluid flowing in the second direction.

A second aspect of the present invention regards an extraction sampler including a chamber, a first filter, and a second filter. The chamber includes an inlet port for receiving a contaminated substance and directing the received contaminated substance to an interior portion of the chamber, and an outlet port in communication with the interior portion and a substance conduit exterior to the chamber. The first filter includes a first channel that extends into the interior portion and has a first end and a second end that extend out of the interior portion. The first channel contains a first fluid and the first channel is permeable to the extent that a first contaminant present in the contaminated substance is conveyed through a first wall defining the first channel and into the first fluid. The second filter includes a second channel that extends into the interior portion and has a third end and a fourth end that extend out of the interior portion. The second channel contains a second fluid and the second channel is permeable to the extent that a second contaminant present in the contaminated substance is conveyed through a second wall defining the second channel and into the second fluid.

A third aspect of the present invention regards an ion mobility sensor system including a first chamber having a first port to receive a fluid exterior of the chamber and a second port to have the fluid leave an interior of the first chamber. The ion mobility sensor system also includes an electrode system that generates an electric field within the interior of the first chamber. The ion mobility sensor system further includes an extraction sampler. The extraction sampler includes a second chamber including an inlet port for receiving a contaminated substance and directing the received contaminated substance to an interior portion of the second chamber, and an outlet port in communication with the interior portion and a substance conduit exterior to the second chamber. Additionally, the extraction sampler includes a filter with a channel that extends into the interior portion and has a first end and a second end that extend out of the interior portion. The channel contains the fluid and the channel is permeable to the extent that a contaminant present in the contaminated substance is conveyed through a wall defining the channel and into the fluid.

A fourth aspect of the present invention regards an ion mobility sensor system including an ion mobility spectrometer that generates a constant electric field in a first direction along the length of the ion mobility spectrometer, a differential mobility spectrometer coupled to the ion mobility spectrometer at an interface region, and a flow operative device. The flow operative device is coupled to the interface region and configured to allow a fluid to be inserted into the interface region. The fluid is divided into a first portion of fluid which flows in a second direction parallel to the first direction and acts as an ion driver for the differential mobility spectrometer, and a second portion of the fluid which flows through the ion mobility spectrometer in a third direction opposite the second direction.

One or more aspects of the present invention provide the advantage of the versatility to use multiple filters with different permeable membranes to allow the permeation of numerous distinct molecules, thereby collecting a plurality of specific contaminants for analysis by the ion mobility sensor system.

One or more aspects of the present invention provide the advantage of providing improved monitoring of chlorinated hydrocarbons in groundwater due to improved resolution and contaminant identification.

One or more aspects of the present invention provides the advantage of being able to operate in ambient atmospheric pressure without the need of a vacuum and can be microfabricated in a compact size.

One or more aspects of the present invention provide the advantageous tandem combination of an IMS spectrometer first followed by a DMS spectrometer. This tandem combination may have an overlapping interface defined as the space between the second B-N gate in the IMS spectrometer and DMS spectrometer entrance electrode. The ion drivers in the IMS spectrometer and DMS spectrometer may be overlapped in the interface region, with the IMS spectrometer ion driver being an electric field and the DMS spectrometer ion driver being a flowing gas. This interface region may be configured so that within this region, an electric field and a gas flow operate jointly to help facilitate the movement of ions from the exit of the IMS spectrometer to the entrance of the DMS spectrometer. The electric field may be in the same direction as the drift field of the IMS spectrometer. The gas flow may be the same flow used to drive ions in the DMS filtration gap towards the second electrode of the DMS spectrometer. This IMS/DMS interface can ensure the transport of ions from the IMS spectrometer exit to the DMS spectrometer entrance without incurring a significant loss of ions.

DETAILED DESCRIPTION OF THE PREFERRED EMBODIMENTS

Except where otherwise indicated, like numbered components in one or more figures are generally constructed in a like manner and generally operate in a like manner.

Figure 1:
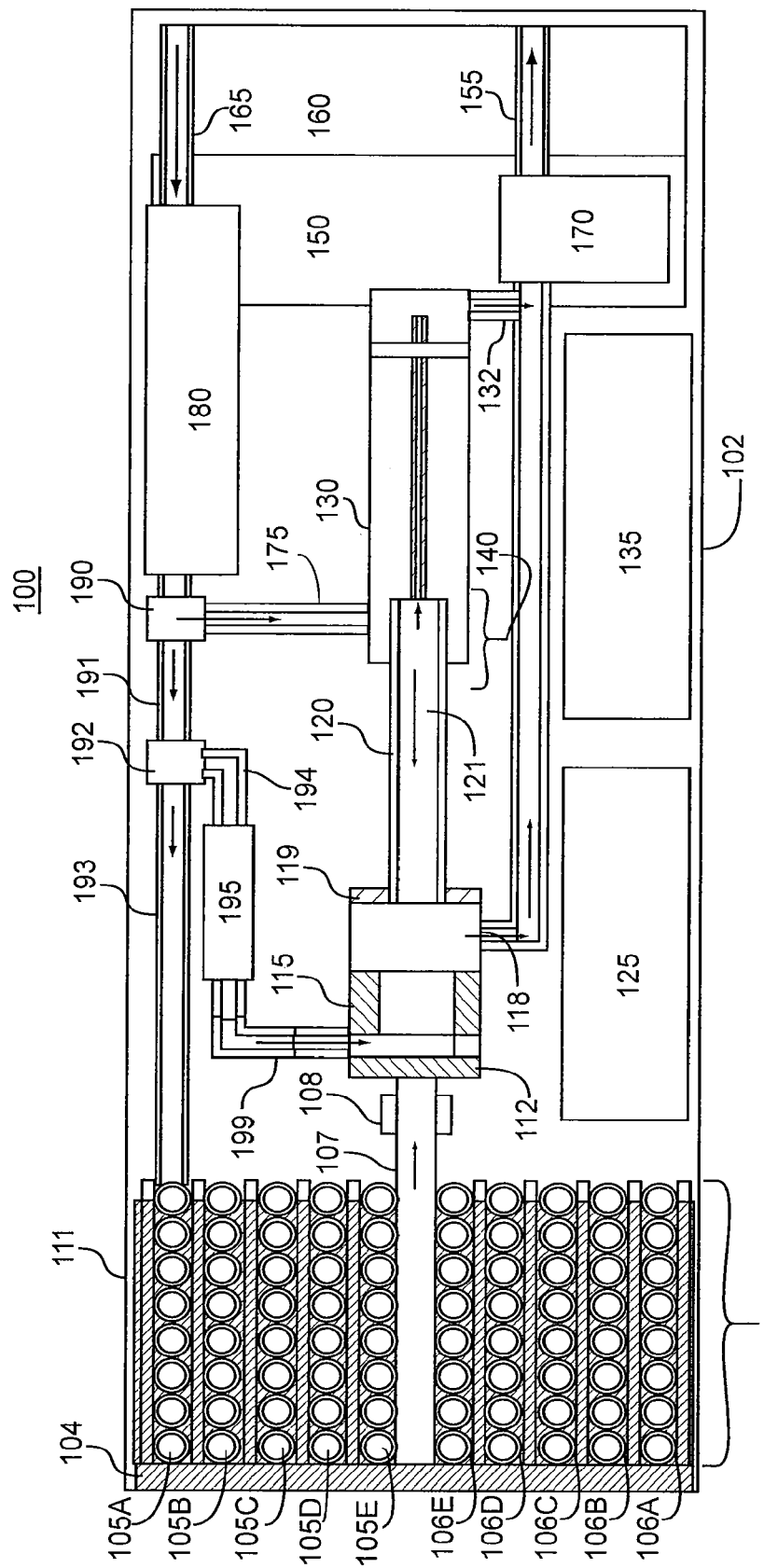
FIG. 1 shows a schematic view of one embodiment of an ion mobility sensor system in accordance with the present invention.

FIG. 1 shows a schematic view of a first embodiment of an ion mobility sensor system 100 in accordance with the present invention. Described generally, in this embodiment, a fluid, which is usually a carrier gas, enters the ion mobility sensor system 100 through channel 165 and is moved indirectly by a flow controller, such as pump 170, via the closed channel system including channels 175, 191, 193, 194, and 199, through a dryer 180, a first flow control unit 190, a channel 191, a second flow control unit 192, and a channel 193 into filters 105A-E of extraction sampler 110. Each filter 105A-E is constructed of a permeable membrane 106A-E. Extraction sampler 110 includes a chamber 111 in communication with a sample substance 104, which is often groundwater. Contaminants in the sample substance 104 permeate through the permeable membranes 106A-E and are carried by the carrier gas flowing in the inner space of filters 105A-E into the inner space of an output channel 107. From the output channel 107, the carrier gas flows through a moisture sensor 108 which ensures that the carrier gas is dry enough to be analyzed. Afterwards, the carrier gas passes through a membrane desorber 112 and into an atmospheric pressure chemical ionization (APCI) chamber 115, wherein ions are formed from the contaminants. A portion of the carrier gas entering the second flow control unit 192 from channel 191 is redirected through channel 194, calibrant container 195, channel 199, and ultimately into the APCI chamber 115 to help facilitate the identification of ions from the carrier gas directed through output channel 107 and moisture sensor 108. These ions formed by the APCI chamber 115 are then injected by a first Bradbury-Nielson (B-N) gate 119 into the drift channel 121 of an IMS spectrometer 120, wherein linear IMS is performed with an electric field applied by the electronics 125 for the IMS spectrometer 120. In linear IMS, ion velocity is linearly related to the IMS drift electrical field. The electronics 125 for the IMS spectrometer 120 record the drift time of the ions travelling between the first B-N gate 119 and a second B-N gate 122 (see FIG. 10). A delay module in the electronics 125 for the IMS spectrometer 120 may be used to selectively permit ions with a desirable traveling time to pass through the linear IMS drift channel 121 and encounter a potential difference existing in the IMS/DMS interface 140.

The IMS/DMS interface 140 (see FIGS. 1 and 10) is configured to allow an IMS spectrometer and a DMS spectrometer to be used together. A portion of the carrier gas passing through dryer 180 is directed by the first flow control unit 190 to enter at or just before the IMS/DMS interface 140 through channel 175, with a first volume of the carrier gas (represented by the left-hand arrows of FIG. 10) being propelled down the drift channel 121 of the IMS spectrometer 120, and a the remaining second volume of the carrier gas (represented by the right-hand arrows of FIG. 10) being propelled down the DMS spectrometer 130. In the IMS spectrometer 120, the carrier gas flow from channel 175 is in the opposite of the ion traveling direction. This reverse flow of carrier gas through the IMS spectrometer 120 is helpful for blocking un-ionized neutral contaminants from entering the drift channel 121 of the IMS spectrometer 120. In the DMS spectrometer 130, the carrier gas flow from channel 175 is in the same direction as the average direction of passing ions. The flow of carrier gas through the DMS spectrometer 130 is helpful as it drives the ions which passed through the IMS/DMS interface 140 through the DMS spectrometer 130. Ions moving into the DMS spectrometer 130 are separated and filtrated by an asymmetric potential waveform 1110 applied to the gap between side electrodes 1120 and 1130 (see FIG. 10). The electronics 135 for the DMS spectrometer 130 supply such an asymmetric potential waveform 1110 and record the ions' compensation voltages, which represent the separation parameter for the DMS spectrometer 130. The compensation voltage refers to the voltage which may be applied by the electronics 135 for the DMS spectrometer 130 which still allows for a particular ion to pass from the entrance electrode 905 to the exit electrode 906 without hitting the side electrodes 1120 and 1130 (see FIG. 12). From the recorded drift times within the IMS spectrometer 120 and compensation voltages within the DMS spectrometer 130, a two-dimensional graph can be created and displayed by the control and signal unit 150 and a battery and driver unit 160, where the graph identifies what contaminants exist in the examined sample substance 104.

Using an IMS spectrometer 120 in conjunction with a DMS spectrometer 130 proves useful. Though use of the IMS spectrometer 120 may, when used with a sample substance contaminated with chlorinated hydrocarbons, prove difficult for providing specificity of particular chlorinated hydrocarbons, the IMS spectrometer 120 is sufficiently capable of separating these chlorinated hydrocarbon ions from larger, unrelated, ions which otherwise may complicate an ion analysis conducted by a DMS spectrometer. These chlorinated hydrocarbon ions, which in a sense have been weeded out by the IMS spectrometer, are then introduced into the DMS spectrometer 130 through the IMS/DMS interface 140.

The IMS/DMS interface 140 may be defined as the space between the second (sometimes referred to as "exit") B-N gate 122 of the IMS spectrometer 120 and the entrance electrode 905 for the DMS spectrometer 130. The present ion mobility sensor system 100 may be operated in positive mode or in negative mode. In either mode, a potential difference may exist between the exit B-N gate 122 and the DMS entrance electrode 905.

In positive mode, the potential at the exit B-N gate 122 is larger than that at the DMS entrance electrode 905, and thus positive ions are swept across the potential difference towards the DMS spectrometer 130. In negative mode, the potential difference between the exit B-N gate 122 and the DMS entrance electrode 905 is negative, so that negative ions are swept across the potential difference towards the DMS entrance electrode 905 of the DMS spectrometer 130, while positive ions are repelled by the electric field.

In either mode of operation, a flow of gas (portion of 180) needs to be applied between the exit B-N gate 122 and the DMS entrance electrode. As such, a combination of the above-described potential difference coupled with the gas flow helps facilitate the movement of ions with desirable polarity through the IMS/DMS interface 140 and into the entrance of the DMS spectrometer 130. Those ions which have passed into the DMS spectrometer 130 are pushed along through the DMS spectrometer 130 by the flow of gas through the DMS spectrometer 130 in a direction from the DMS entrance electrode 905 to a second DMS electrode 906 (see FIG. 8). During this general movement, the electronics 135 for the DMS spectrometer 130 applies a periodic asymmetric waveform 1110 (see FIG. 12) which attracts the ions to the side electrodes 1120 and 1130. By measuring the compensation voltages, the ion mobility sensor system 100 can be used to separate out each of the chlorinated hydrocarbon ions and delineate which chlorinated hydrocarbon contaminants exist in the liquid analyzed. In this way, the combination of the IMS spectrometer 120 and the DMS spectrometer 130 can prove useful for a number of applications, including groundwater analysis.

While described periodically in this disclosure as an IMS/DMS combination, in some embodiments, the ion mobility sensor system 100 can be switched to operate in an IMS-only mode as well. In such circumstances, the DMS entrance electrode 905 is used as the charge collection plate. Due to the absence of the flow through the DMS, most ions out of the second B-N gate 122 cannot transport to the DMS spectrometer 130 and reach electrode 905, generating ion current for an IMS response.

Looking now more specifically at the ion mobility sensor system 100 of FIG. 1, the ion mobility sensor system 100 may be enclosed by a housing 102, which may encompass all of the components described above, except for part or all of the sample substance 104, which may instead be in communication with the housing 102. Additionally, the housing 102 includes a control and signal unit 150 and a battery and driver unit 160. While the embodiment in FIG. 1 shows the entire ion mobility sensor system 100 as being enclosed by the housing 102, other embodiments may be created where a portion or portions of the ion mobility sensor system 100 exist outside of housing 102. Alternatively, in one embodiment, no part of the ion mobility sensor system 100 is enclosed by the housing 102.

The entire ion mobility sensor system 100 may be any size, but preferably is around or less than 30 cm in length. This provides the advantage of being small, minimizing power consumption and space while still providing sufficient analysis.

The housing 102 of ion mobility sensor system 100 may be placed in the ground, wherein it may be surrounded by a sample substance 104 such as underground water, mud, clay, liquid conduit, or other fluid. With the exception of openings for the sample substance 104 to come into and out of the ion mobility sensor system 100 through channels 155 and 165, as well as an inlet port 220 and an outlet port 230 in the extraction sampler 110, the housing 102 is generally sealed from outside elements. As such, the housing 102 is made of a material of sufficient durability so as to allow the ion mobility sensor system 100 to be used for long period of time underground without degrading or requiring repair, while also preventing moisture to seep into the electrical components of the ion mobility sensor system 100. Examples of such materials for the housing include, but are not limited to, glass, plastics, metals, fiberglass, or rubber.

Alternatively, the ion mobility sensor system 100 inside of the housing 102 may be placed above ground wherein it may be surrounded by a sample substance 104 such as a fluid such as air or vapor, or may be placed anywhere else where it may be surrounded by a sample substance 104 capable of containing contaminants which may be analyzed by a IMS spectrometer and a DMS spectrometer.

A fluid, which is often air or another carrier gas, first enters the ion mobility sensor system 100 at channel 165. Ideally the fluid is a gas, though the fluid may be a gas other than dry air. The fluid may be a vapor. In some embodiments, the fluid may also be any combination or variation of the above-described gas and vapor.

The entry of this carrier gas into the ion mobility sensor system 100 may be aided by suction provided from the pump 170. While the flow controller in FIG. 1 is pump 170, alternatively or additionally, flow controller may be any system or device capable of controlling, propelling, moving, or propagating the flow of a fluid. Pump 170 may force the flow of the carrier gas throughout all or part of the ion mobility sensor system 100.

The carrier gas entering the ion mobility sensor system 100 travels through channel 165 and into a dryer 180. The purpose of dryer 180 is to remove moisture from the incoming carrier gas and to block any air moisture from entering further into the ion mobility sensor system 100. In one embodiment, the dryer 180 may be a commercial product that includes a mole sieve and activated charcoal.

Carrier gas which passes through the dryer 180 is sent into the first flow control unit 190. The first flow control unit 190 controls the carrier gas so as to provide an air flow with desirable flow rates. A portion of the incoming carrier gas from dryer 180 is directed by the first flow control unit 190 through channel 175 into the IMS/DMS interface 140, and will be discussed in more detail later. In an alternative embodiment, channel 175 is connected to the IMS spectrometer 120 near the IMS/DMS interface 140. The rest of the carrier gas is sent by first flow control unit 190 through channel 191 into a second flow control unit 192. The second flow control unit 192 acts in the same general manner as the first flow control unit 190, sending a portion of the incoming carrier gas through channel 194 into the calibrant container 195, through channel 199, and ultimately into the APCI chamber 115, a process which also will be discussed later. The remainder of the incoming air is sent by the second flow control unit 192 through channel 193 and directed into the filters 105A-E of the extraction sampler 110.

The ion mobility sensor system 100 includes an extraction sampler 110 in communication with a sample substance 104 that may contain contaminants. The extraction sampler 110 shown in FIG. 1 includes a chamber 111, five filters 105A-E each made of a permeable membrane 106A-E, and an output channel 107. Though the extraction sampler 110 shown in FIG. 1 has five filters 105A-E, the extraction sampler 110 may have more or fewer filters as desired.

Figure 2:
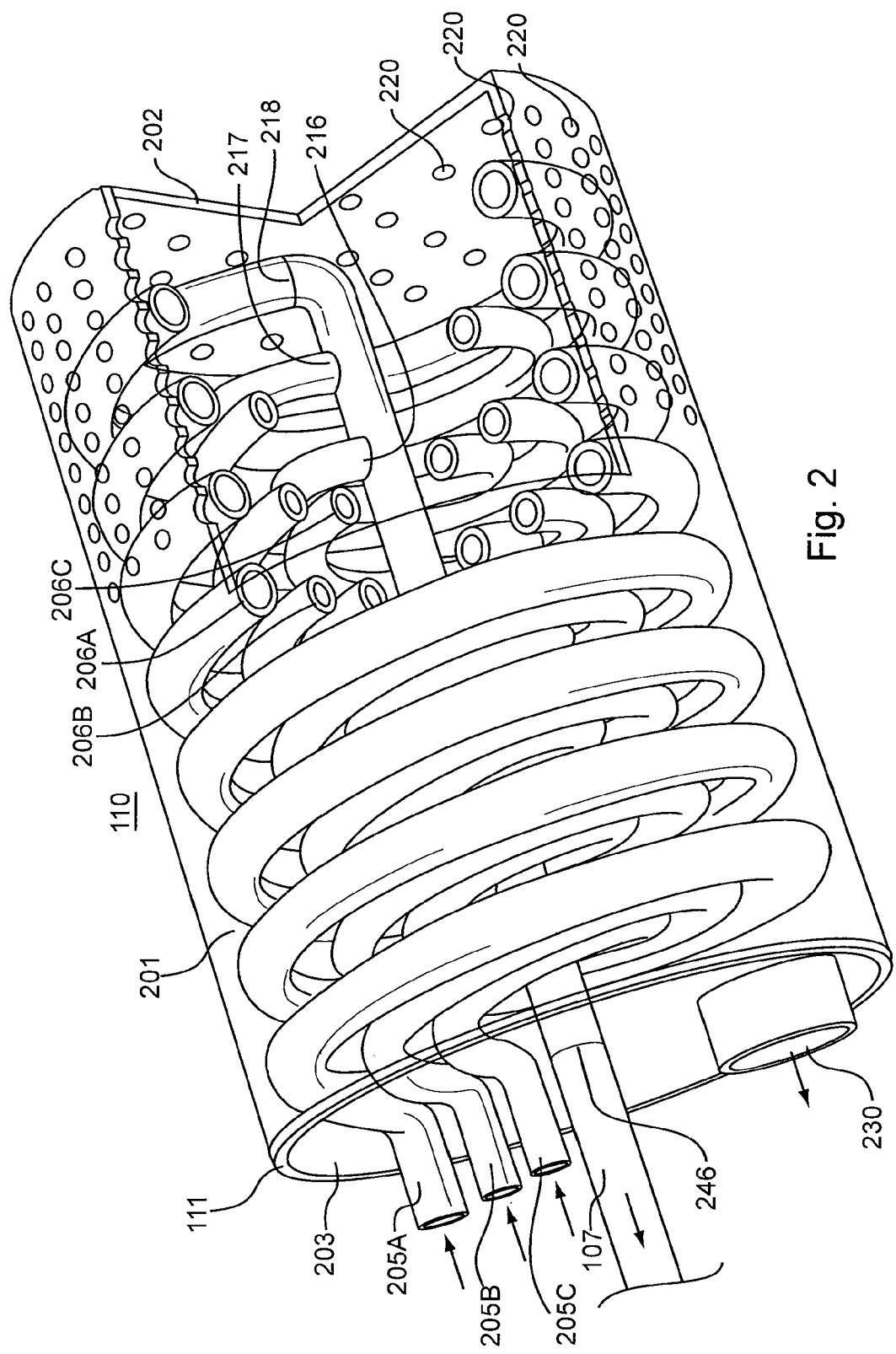
FIG. 2 shows a first embodiment of an extraction sampler to be used with the ion mobility sensor system of FIG. 1 in accordance with the present invention.

FIG. 2 shows an alternative embodiment of an extraction sampler 110 for use in the ion mobility sensor system 100. The extraction sampler 110 in FIG. 2 has only three filters 205A-C. The filters 105A-E and filters 205A-C operate in generally the same manner. In all other substantive ways aside from the number of filters included, the extraction samplers 110 of FIG. 1 and FIG. 2 contain the same features and components (even if only numbered in one of the figures) and operate in generally the same manner, with all like numbered components having the same characteristics in both embodiments. With the above understanding in mind, the discussion to follow will regard the extraction sampler of FIG. 2 and is applicable to the extraction sampler of FIG. 1.

In one embodiment, the extraction sampler 110 is configured to collect contaminants from a fluid such as groundwater. Broadly, this is accomplished by placing the extraction sampler 110 (either together with the rest of the ion mobility sensor system 100 or apart) in a well or sampling of ground water sufficient to allow water to enter chamber 111 through inlet ports 220. Meanwhile, carrier gas such as dry air flows through the filters 205A-C made of permeable membranes 206A-C and into the output channel 107, where it is eventually fed into the moisture sensor 108. The permeable membranes 206A-C are constructed so as to allow certain molecules, compounds, chemicals, elements, analytes, or contaminants (collectively referred to hereinafter as "contaminants") to pass through them from the groundwater or other sample substance 104. These contaminants are swept up in the carrier gas flowing through the filters 205A-C and carried into and through output channel 107 and into the remainder of the ion mobility sensor system 100.

Though depicted in FIG. 1 as a component of the ion mobility sensor system 100, the extraction sampler 110 may alternatively be configured for use with any number of analyzing devices capable of analyzing a component or product of a carrier gas. These devices include, but are not limited to, an IMS-only system, a DMS-only system, a DMS-first, IMS-second combination system, aspiration analyzers, and an IMS-first, MS-second system.

More specifically, as shown in FIG. 2, the chamber 111 of the extraction sampler 110 has a cylindrical shape. The chamber 111 is defined by a cylindrical outer wall 201, which is connected on each end to circular walls 202 and 203 that act to generally enclose the cylindrical outer wall 201. The chamber 111 may be configured to have any dimensions. Preferably, the chamber 111 has the same diameter as the diameter of the ion mobility sensor system housing 102, but this is not required. In one embodiment, the diameter of the chamber 111 and the diameter of the ion mobility sensor system body are both 10 cm. The chamber 111 may be configured to have a length of any size. In a preferred embodiment, the chamber 111 has a length of approximately 10 cm. While the chamber 111 shown in FIG. 2 has a cylindrical shape, other closed shapes, such as a rectangular box or pyramid, or other dimensions of any such shape, are possible.

The walls 201, 202, and 203 which define chamber 111 of extraction sampler 110 may be made of any material or combination of materials which is sufficient to generally contain underground water except at any inlet or outlet ports. In one embodiment, the chamber 111 is made of a material of sufficient durability so as to allow the extraction sampler 110 to be used for long period of time underground without degrading or requiring repair. Examples of such materials include, but are not limited to, glass, plastics, metals, fiberglass, or rubber. Additionally, the walls may exude any level of transparency and be of any thickness sufficient to protect the chamber 111.

With continued reference to FIG. 2, the chamber 111 of the extraction sampler 110 has a number of inlet ports 220 that are in communication with sample substance 104. Each inlet port 220 is ideally configured to allow a contaminated liquid, such as groundwater, to enter the interior of the chamber 111. The extraction sampler 110 may include one inlet port 220 configured to allow a fluid to flow into the chamber 111, or alternatively may include multiple inlet ports 220, as shown in FIG. 2. The inlet ports 220 may be of any size or dimension, and may be placed along the cylindrical wall 201 of the chamber 111 (or any side wall of the chamber 111), or along circular wall 202 at one end of chamber 111, or in any combination thereof.

The chamber 111 also has one or more outlet ports 230. Each outlet port 230 is ideally configured to allow any sample substance 104 which is inside chamber 111 to escape out of the chamber. The extraction sampler 110 may include one outlet port 230, or alternatively may include a plurality of outlet ports 230. The opening or openings may be of any size or dimension, and may be placed along the cylindrical wall 201 of the chamber 111 (or any side wall of the chamber 111), or along circular wall 203 at one end of the chamber 111, or in any combination thereof.

As indicated by the arrows in FIG. 2, sample substance 104 (in FIG. 2, water) in communication with the extraction sampler 110 enters chamber 111 through the inlet ports 220 and exits chamber 111 through the outlet port 230. In this way, chamber 111 is ideally continuously filled with a sample substance 104, which regularly flows through the chamber 111.

In some embodiments, the inlet port 220 of chamber 111 is connected to another structure which feeds the sample substance 104 into the chamber 111. In such an embodiment, the outlet port 130 may or may not be connected to another structure to facilitate the removal of the sample substance 104 from the chamber 111.

While the ion mobility sensor system 100 of FIG. 1 only shows one extraction sampler 110, in some embodiments multiple extraction samplers may be used in any number of ways. For example, in one embodiment, carrier gas which leaves a first extraction sampler may be directed via a structure such as an output channel 107 directly into the inlet port 220 of a second extraction sampler, which will filter the contaminants a second time before the contaminants are moved into the remainder of the ion mobility sensor system. Any number of extraction samplers may be used in series like this, with the carrier gas 104 with the filtered contaminants of the previous extraction sampler 110 passing out of the previous extraction sampler and into the inlet port of the next extraction sampler. Additionally or alternatively, any number of extraction samplers 110 may be used in parallel with each other, or in any combination of parallel and series. Each extraction sampler 110 used in such a manner may be the same as other extraction samplers 110 used in series or parallel, or may be different from some or all of the other extraction samplers 110.

This sample substance 104, in one embodiment, may be contaminated groundwater. Alternatively, the sample substance 104 may be well water, tap water, lake or river water, groundwater, or other water, any or all of which may or may not include some level of contamination. Alternatively, the sample substance 104 may be any liquid or combination of liquids of any chemical makeup, consistency, or type, such that the liquid or combination of liquids is capable of flowing through the extraction sampler 110. Alternatively, the sample substance 104 may be soil, clay, mud, dirt, air, gas, vapor, or fumes. Ideally, sample substance 104 is capable of including contaminants which are measurable by ion mobility sensor system 100.

Each of the three filters 205A-C shown in FIG. 2 is preferably made of a cylindrical tube that is formed in the shape of a helix. The helix may have a density of approximately 2 turns per centimeter, or alternatively may have a density of any number of turns per centimeter. Furthermore, the cylindrical tube may have a diameter of ranging from 0.1 cm to 0.5 cm, and thickness ranging from 0.01 cm to 0.05 cm. As shown in FIG. 2, the three filters 205A-C are formed to be concentric about a central longitudinal axis of the chamber 111.

As shown in FIG. 2, at the ends of each filter 205A-C are formed straight portions that extend parallel to the central longitudinal axis of chamber 111. These ends enter the chamber 111 by passing through openings in the circular wall 203.

While the main shape of a filter 205 may be helical, as shown in FIG. 2, it may alternatively be formed in any other shape or design. For example, the filter may be a long and straight cylindrical tube which travels through the chamber. Alternatively, the filter may zig-zag back and forth through the interior of a chamber. Alternatively, the filter may be a flat shape with a carrier gas for removing permeates. Alternatively or additionally, the shape of the filter may be any shape or design or combination of geometrical or other shapes and designs. A helical shape may increase permeation rates, but so may a number of other shapes.

The filters 205A-C shown in FIG. 2 each have circular cross-sections. It should be appreciated that these filters may take on any cross-section. A filter's cross-section may be shaped in any geometrical or other shape, such as a square, rectangle, or triangle. The filter's cross-section may vary along the filter's length in both shape and/or size. For example, the filter may be shaped like an accordion, wherein the cross-section is always circular, but the diameter varies along the length of the filter. Alternatively, the cross-section may be circular at one end, square at a second end, and blended between the two shapes in between the two ends. Additionally or alternatively, the cross-section of the filter may be a number of shapes at different points along the filter's length, and may vary in any number of fashions along that length.

Also, it should be appreciated that, while the embodiment of FIG. 2 shows three filters and the embodiment in FIG. 1 shows five filters, any number of filters may be used in any combination. More filters may be added, for example, to allow collection of a wider variety of contaminants, or fewer may be used as needed or desired.

Referring again to FIG. 2, each of the filters 205A-C of extraction sampler 110 includes, at least in part, permeable membranes 206A-C, such as poly-dimethylsiloxane (PDMS), zeolite-filled poly-dimethylsiloxane, nitrile-butadiene rubber, polybutadiene, and ethylene-propylene terpolymer (EPDM). Generally, the permeable membranes 206A-C of filters 205A-C act as a barrier, allowing only certain contaminants to permeate from a sample substance 104 into the carrier gas flowing through each of the filters 205A-C.

In the case where the sample substance 104 is a liquid, the permeation of contaminants between the sample substance 104 and permeable membranes 206A-C takes place according to Henry's Law, which states that at a constant temperature, the amount of a given gas dissolved in a given type and volume of liquid is directly proportional to the partial pressure of that gas in equilibrium with that liquid. The contaminants are transported by diffusion to the membrane/carrier gas interface wherein they partition into the carrier gas flowing within the filters 205A-C. The process may be easily enacted because the permeability of the permeable membranes 206A-C to volatile organics is many orders of magnitude higher than for air or water. If only a few contaminants are to be monitored, the permeable membrane composition can be optimized for high permeability and resulting sensitivity.

In one embodiment, several permeable membranes are operated in parallel, each with functionality that gives high permeability for selected species.

In one embodiment, a filter 205A-C may include multiple layers of permeable membranes 206A-C, such that contaminants may need to pass through more than one permeable membrane before moving into the IMS spectrometer 120.

In the preferred embodiment, each of the filters 205A-C includes a different permeable membrane with differing physical characteristics to allow different contaminants to permeate through each of the filters 205A-C. For example, filter 205A could include a permeable membrane 206A made of PDMS which has a certain permeability to allow a first class of contaminants such as volatile organic compounds (VOCs) to permeate into the carrier gas, filter 205B could include a permeable membrane 206B made of PDMS which has a different permeability to allow a second class of contaminants such as trichloroethylene (TCE) to permeate into the carrier gas, and filter 205C could include a permeable membrane 206C made of EPDM which has a certain permeability different than those of filters 205A-B to allow a third class of contaminants to pass therethrough. In this way, the permeable membranes 206A-C each allow different contaminants to permeate through the permeable membranes, and in that manner collect multiple contaminants of interest while limiting the introduction of unwanted compounds into a carrier gas inside each filter 205A-C. Each filter 205A-C may be configured so as to allow one or more than one contaminant to permeate from the contaminated groundwater into the filter. In an alternative embodiment, the permeable membranes 206A-C are all constructed in the same general manner and have the same general characteristics and permeability. Alternatively, one or more of the filters may have permeable membranes which are made of the same general material while one or more different filters have permeable membranes made in a different manner or having different general characteristics and permeability. Additionally, the filters 205A-C with permeable membranes 206A-C are not limited to use with contaminated groundwater, but instead may be used for the purposes of separating any type of molecule, chemical, analyte, or compound from any type of fluid. Examples of contaminants to be filtered may include chlorinated hydrocarbons, perchlorate, explosives, chemical warfare agents, and toxic industrial compounds.

The permeable membranes 206A-C of filters 205A-C ideally have a continuous thickness of between 0.01 cm and 0.05 cm. Alternatively, the thickness of the permeable membranes may be increased or decreased as desirable, and may be varied throughout the length of the filter. Each filter 205A-C may have permeable membranes 206A-C with the same or different thicknesses.

In one embodiment, permeable membranes 206A-C include the wall of the filters 205A-C themselves. In an alternate embodiment, the permeable membranes may only be included in a portion of a filter, while the rest of the filter is made from a non-permeable material. In yet another alternative embodiment, portions of the filter are made from a combination of one or more types of permeable membranes and non-permeable membranes. A filter may alternatively be made according to any combination of the above embodiments.

Figure 3A:
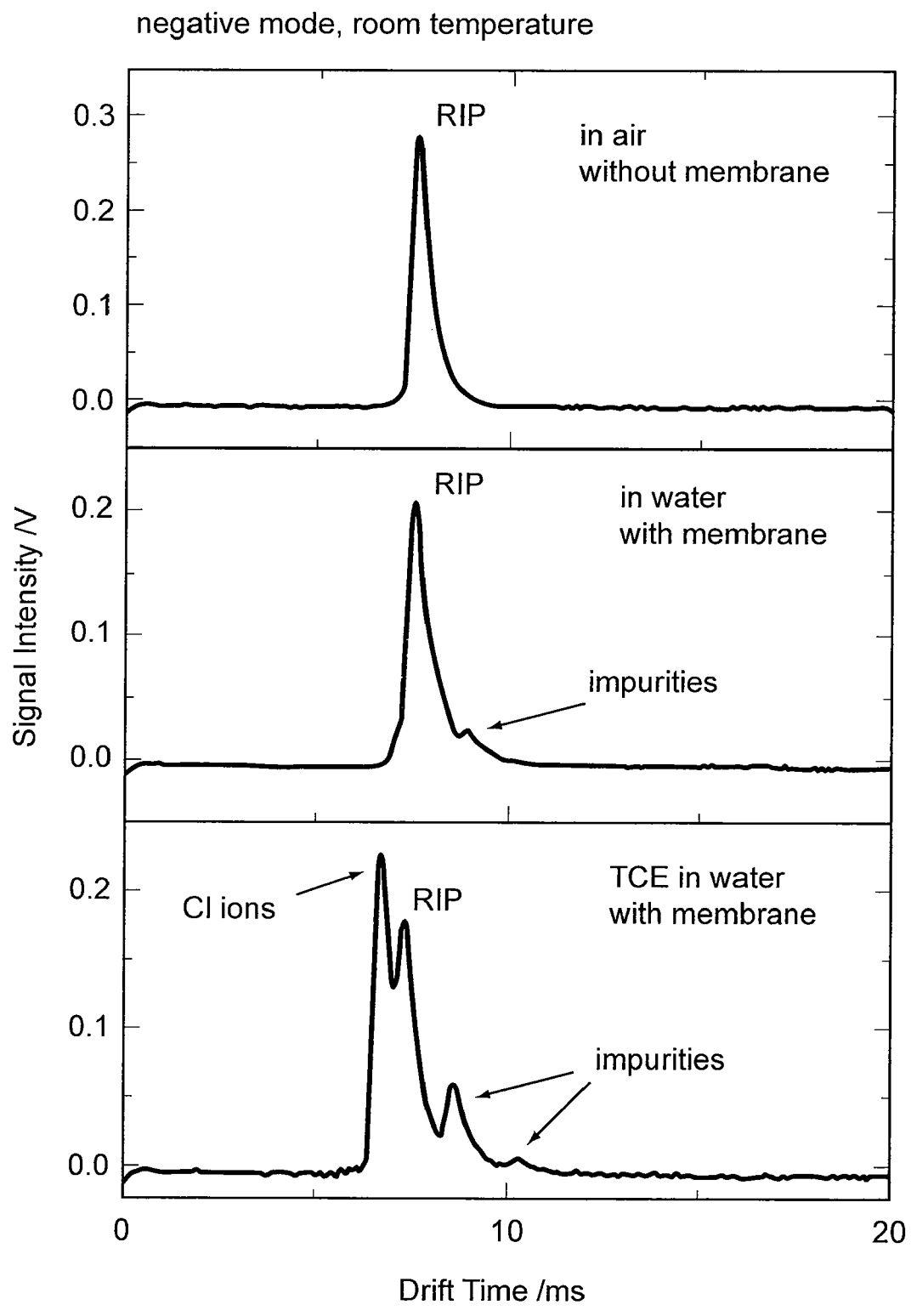
FIG. 3A shows a first possible set of three graphs displaying IMS analysis results for a fluid.

FIG. 3A shows three graphs of a sample analysis of air by the ion mobility sensor system 100 operating in IMS-only negative mode. The topmost graph shows an analysis of dry air, the middle graph shows an analysis of air used as a carrier gas and passed through an extraction sampler 110 surrounded by relatively clean water, and the bottommost graph shows an analysis of air used as a carrier gas and passed through the extraction sampler 110 surrounded by water contaminated with TCE, where the carrier gas when analyzed included negative ions from the TCE. RIP in these graphs refers to the reactant ion peak. The middle graph, wherein clean water was sampled, shows that the extraction sampler 110 gathered very few impurities. However, as shown by the bottommost graph, the extraction sampler 110 was successful in gathering multiple contaminants and impurities for subsequent analysis.

Figure 3B:
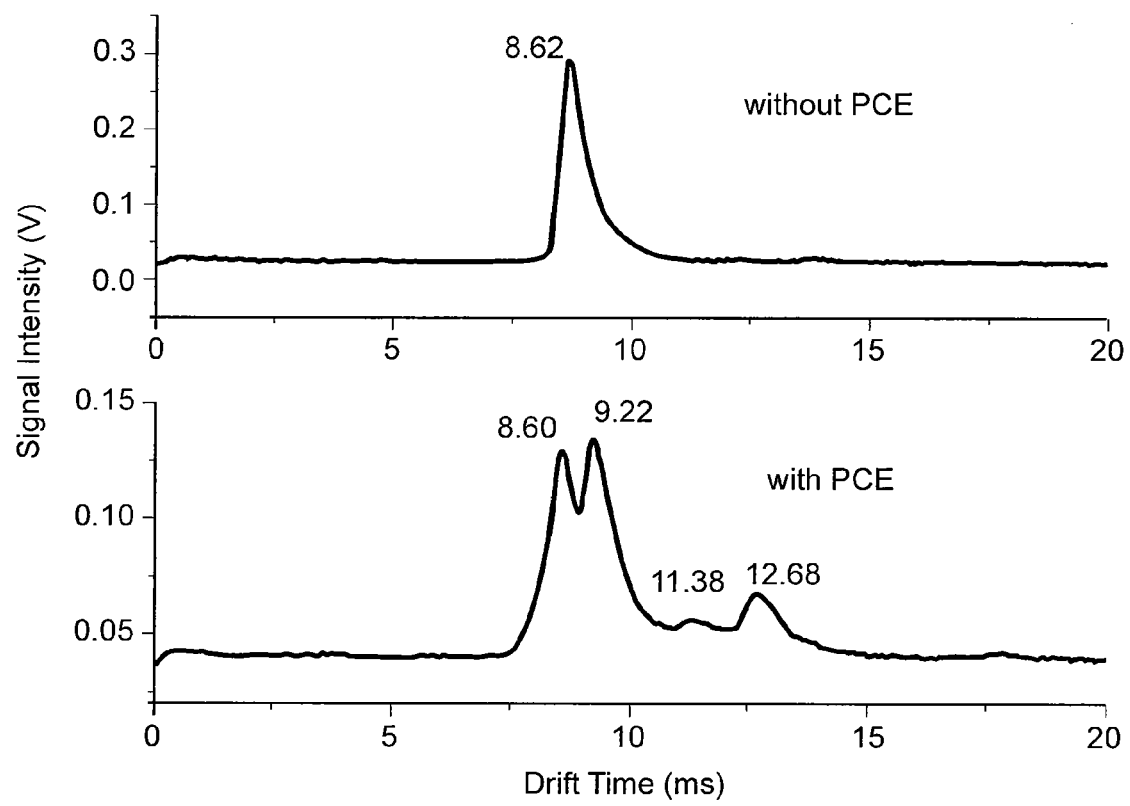
FIG. 3B shows a second possible set of two graphs displaying IMS analysis results for a fluid.

FIG. 3B illustrates two additional sample analysis results using the ion mobility sensor system 100 operating in IMS-only positive mode. In each of the samples used, the positive ions of tetrachloroethene (PCE) were analyzed by the ion mobility sensor system. The topmost graph shows the results of analyzing air used as a carrier gas and passed through the extraction sampler 110 surrounded by water without any substantial quantities of PCE. The bottom graph shows the results of analyzing air used as a carrier gas and passed through the extraction sampler 110 surrounded by water contaminated with PCE. The exemplary graphs shown in FIG. 3B additionally show that the extraction sampler 110 is successful in gathering multiple contaminants and impurities from contaminated water.

The rate of permeation through the permeable membranes 206A-C may play a factor in determining how to interpret results of any analysis later conducted by, for example, the IMS spectrometer 120. Generally speaking the following calculations may model the permeation rate for the permeable membranes, where C is the concentration of a contaminant in water, N is the concentration of a contaminant as shown through IMS, P is the permeation rate, and f is the flow rate.

$$dC/dt = -P*C \tag{1}$$

$$dN/dt = P*C - f*N \tag{2}$$

$$C = C_0 e^{-P*t} \tag{3}$$

$$N = ((P*C)/(f-P))*(e^{-P*t} - e^{-f*t}) \tag{4}$$

Figure 4:
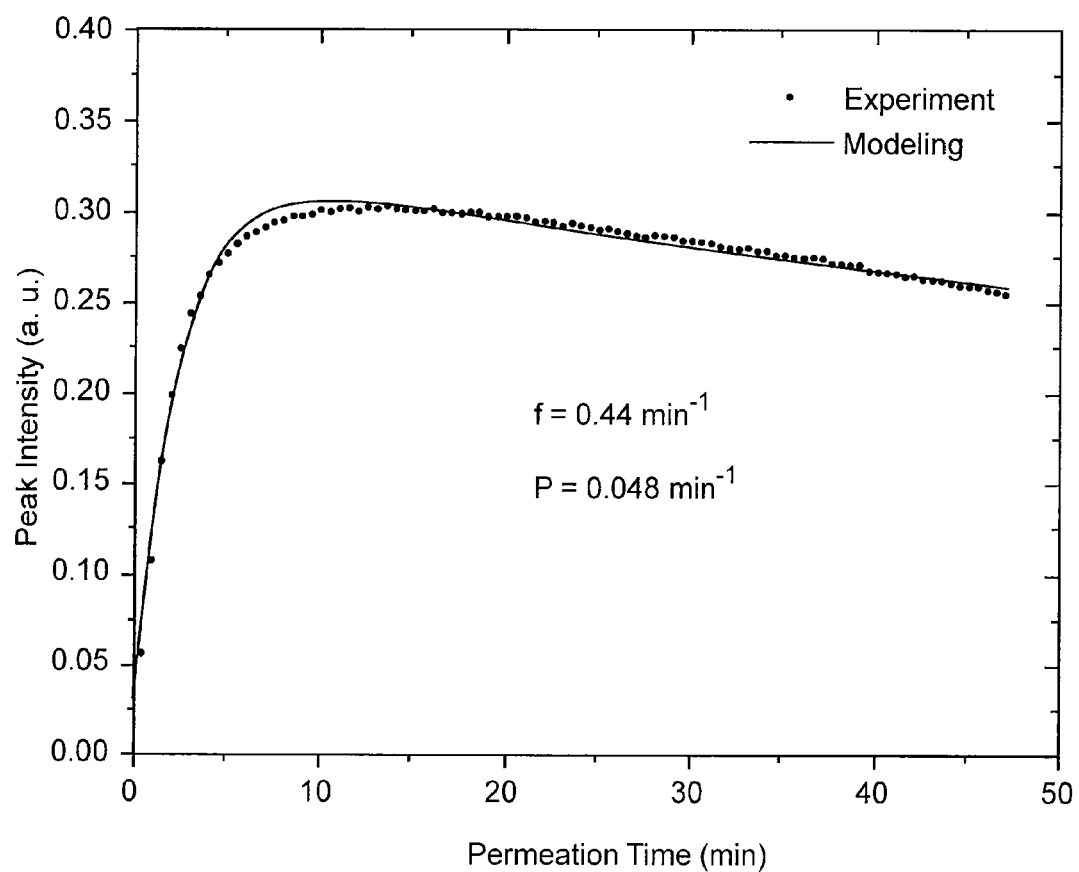
FIG. 4 illustrates one example of an experimental analysis of peak ion intensities measured over permeation times.

As such, in one embodiment, the peak intensity of the contaminant analyzed by an IMS spectrometer 120 may vary with the permeation time. FIG. 4 illustrates one example of an experimental analysis of peak ion intensities measured over permeation times. The results of FIG. 4 correspond to circumstances where $f=0.44$ $min^{-1}$ and $P=0.048$ $min^{-1}$. As shown by FIG. 4, a carrier gas may be sensitive to quantitative analysis, and as such, more accurate results may be achieved if the flow of carrier gas remains constant through the entire analysis period.

Figure 5:
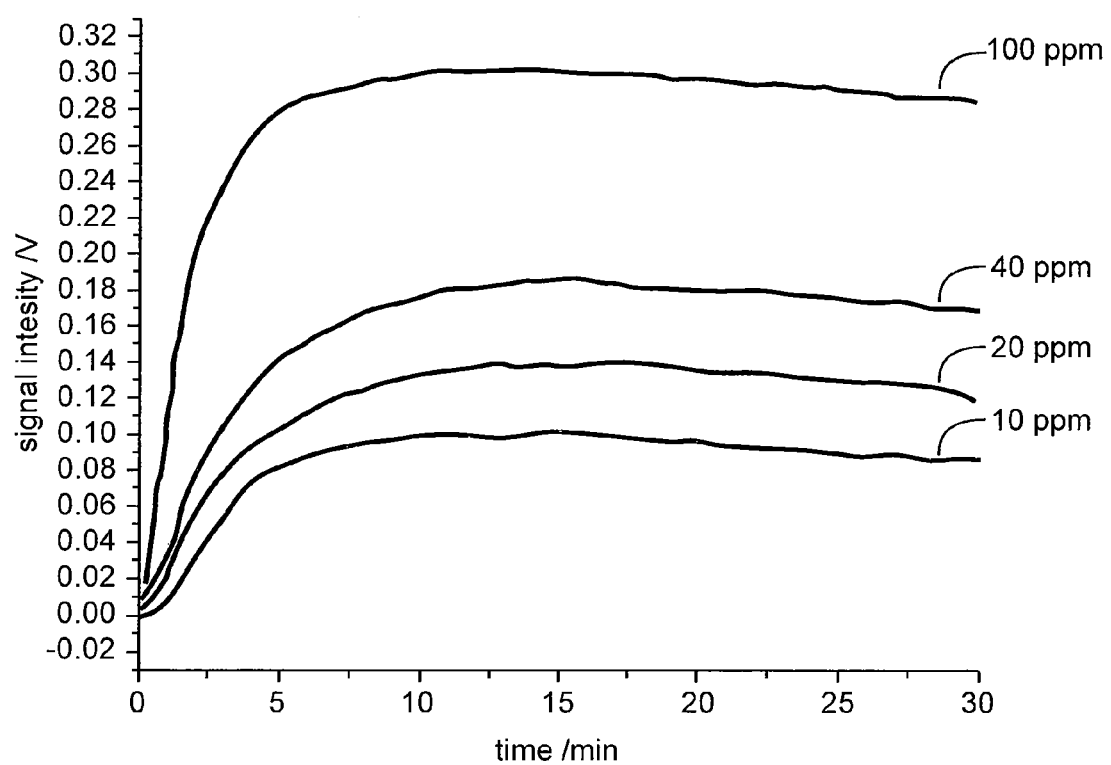
FIG. 5 shows multiple examples of experimental analysis showing the peak ion intensities of contaminants over permeation times for a number of water samples with varying levels of contamination.

FIG. 5 shows multiple examples of experimental analysis showing the peak ion intensities of contaminants over permeation times for a number of water samples with varying levels of contamination. Each of the curves in FIG. 5 represent a water sample having a different level of contamination, ranging from 10 parts per million ("ppm") up to 100 ppm. The results of FIG. 5 show that the shape of the peak intensity curve over permeation time does not appear to vary much with differing peak intensities, but rather appears to simply shift up or down depending on the level of contamination existing in the sampled substance. As such, it may be preferable to conduct analysis on a time-profile basis, rather than at a specific time.

Figure 6:
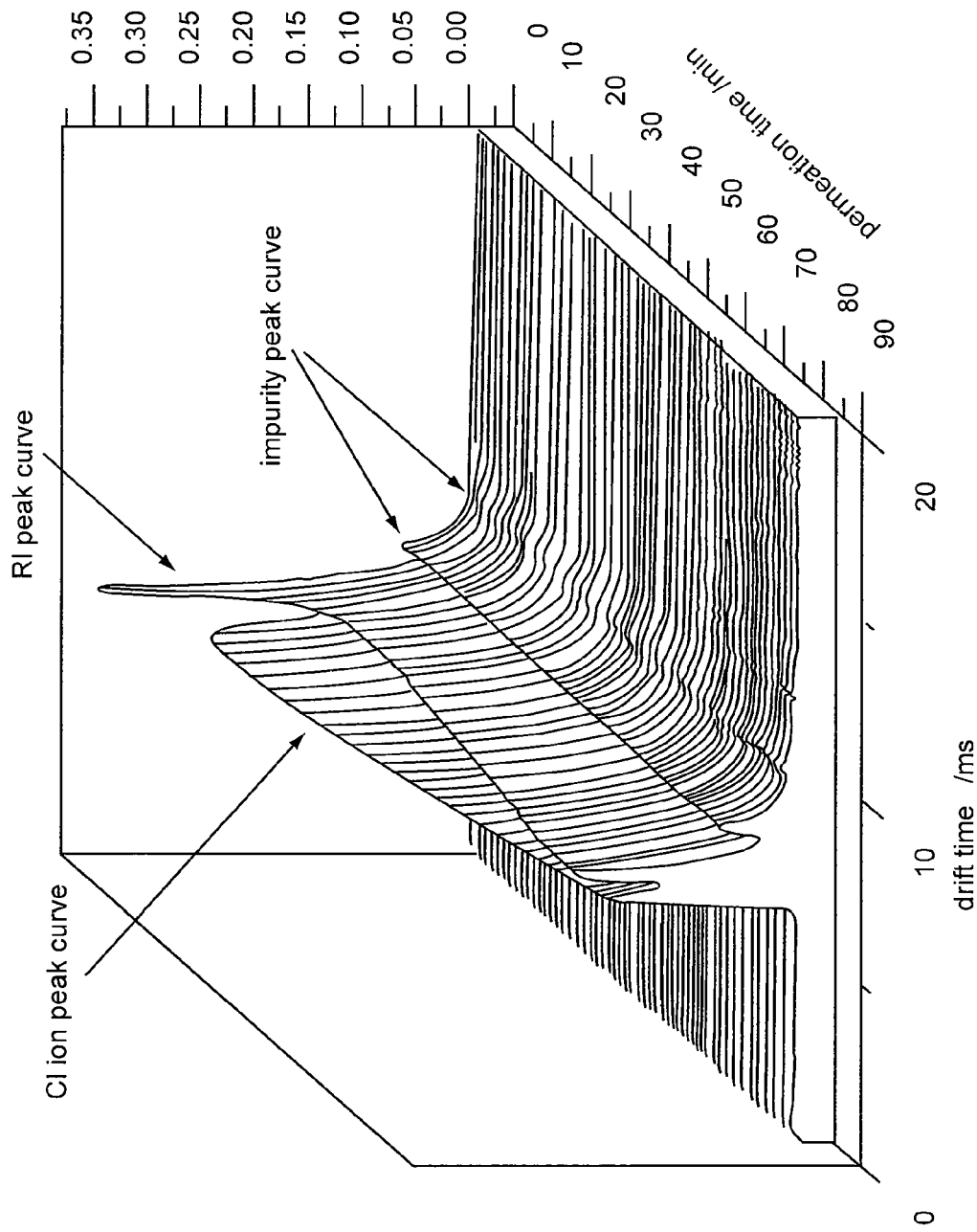
FIG. 6 illustrates the results of a contaminant analysis of a fluid as a function of both permeation time and drift time.

FIG. 6 illustrates how a spectrum analysis of contaminants in one sample substance 104 varies over permeation times. FIG. 6 is the equivalent of a series of snapshots like any one of the three graphs in FIG. 3A or two graphs in FIG. 3B, each snapshot being taken at a different permeation time and stacked together. If one follows the Cl ion peak curve over the permeation time, the same shape as shown in FIGS. 4 and 5 occurs. In this way, one may observe the changes which occur in the contamination analysis as a function of both permeation time (as in FIGS. 4 and 5) and drift time (as in FIGS. 3A-B).

Referring back to the embodiment shown in FIG. 2, each of the three filters 205A-C is connected to an output channel 107. Filter 205A connects to the output channel 107 at connection point 216. Filter 205B connects to the output channel 107 at connection point 217. Filter 205C connects to the output channel 107 at connection point 218. Alternatively, the joining of one or more filters in extraction sampler 110 may occur outside of chamber 111. Alternatively, the filters of an extraction sampler 110 do not have to join at all. In this latter situation, the filters may enter a chamber through one entry point and may exit the chamber at a second, distinct exit point. Each filter may have their own entry points and exit points, or may share an entry point or exit point, or may include some combination of the two. In such circumstances, the extraction sampler 110 may not have an output channel 107. Instead, each filter may join with the remainder of the ion mobility sensor system 100 independently. In other embodiments, an output channel 107 may exist for the joining of some, but not all of the filters. Alternatively, multiple output channels may exist to allow different combinations of filters to join with various combinations of output channels.

In the embodiment of FIG. 2, the output channel 107 exits the chamber 111 at exit point 246, and is configured so that it may be coupled to the IMS spectrometer 130 (shown in FIG. 1) for ion analysis.

The output channel 107 is shown in FIG. 2 as a roughly cylindrical tube of similar dimensions as the filters 205A-C. The output channel 107 may be configured in a manner similar to how the filters 205A-C are configured. In a preferred embodiment, the output channel 107 may be a Swagelok tube.

As previously stated, in the preferred embodiment, a carrier gas flows through filters 205A-C and into the output channel 107. Preferably, the carrier gas flowing through filter 205A is of the same type as the carrier gas flowing through filters 205B and 205C, and preferably is dry air. However, each of the filters 205A, 205B, and 205C may have a carrier gas of a different and distinct type or chemical composition flowing through them. Alternatively, the carrier gas flowing through one or more filter (for example, filters 205A and 205B) may be of the same type while carrier gas flowing through other filters (for example, filter 205C) may be of a different type. Any combination or variation of different carrier gases or fluid types in any combination of filters is possible.

Figure 7:
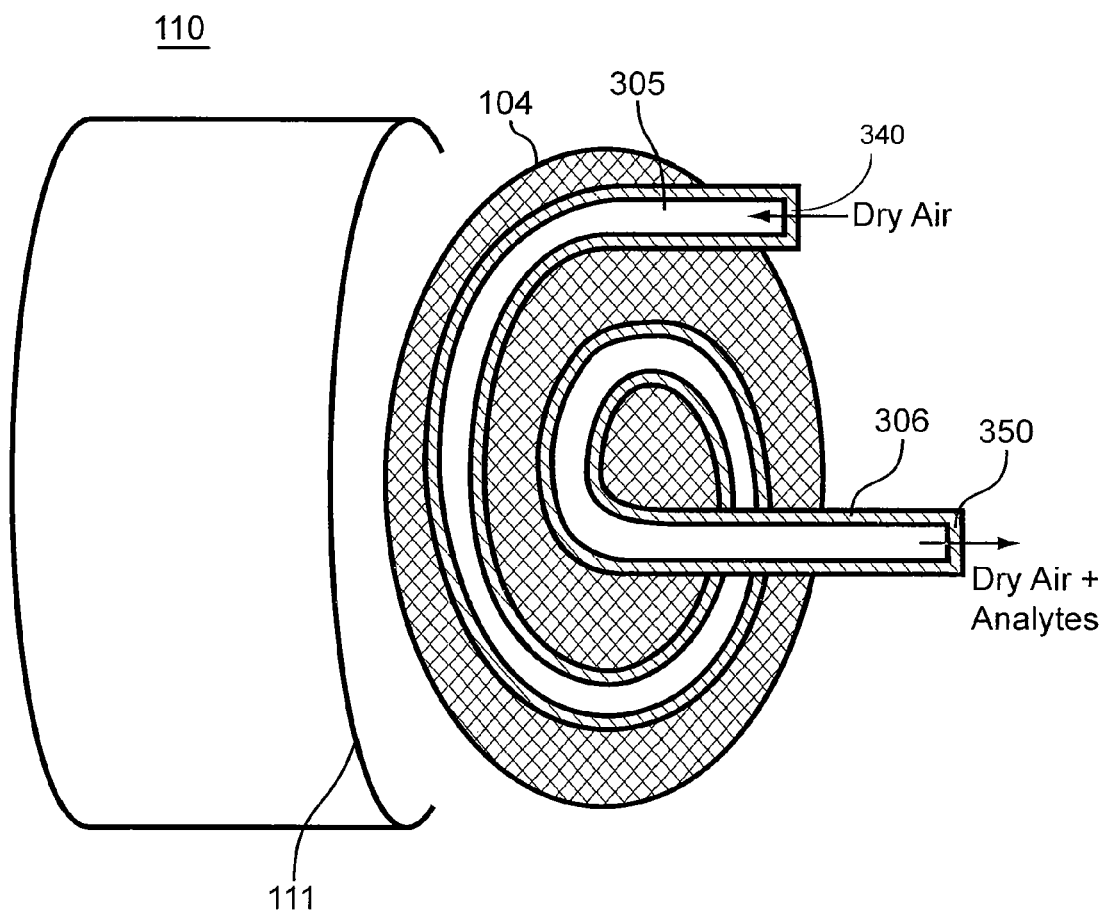
FIG. 7 shows an exploded and schematic view of a second embodiment of an extraction sampler with one filter to be used with the ion mobility sensor system of FIG. 1 in accordance with the present invention.

FIG. 7 shows an exploded view of one embodiment of an extraction sampler 110 with one filter 305 to be used with the ion mobility sensor system 100 of FIG. 1. The extraction sampler 110 shown in FIG. 7 is constructed and operates in a manner similar to the construction and operation of the extraction sampler 110 shown in FIG. 2, with a few differences. The main structural differences between the two embodiments are that the extraction sampler 110 in FIG. 7 has only one filter (305) and no output channel 107, while the extraction sampler 110 in FIG. 2 has three filters (205A-C) and an output channel 107.

Extraction sampler 110 in FIG. 7 includes a chamber 111 filled with sample substance 104. The filter 305, which is generally the same in makeup and function as the filters 105A-E and 205A-C previously discussed, has a permeable membrane 306, which is generally the same in makeup and function as the permeable membranes 106A-E and 206A-C previously discussed. The filter 305 also has an entrance end 340, and an exit end 350, each of which are located outside of chamber 111, while a portion of the filter 305 between the ends is located inside of the chamber 111 and is generally surrounded by sample substance 104. When used instead of the extraction sampler 110 of FIG. 1, the extraction sampler 110 of FIG. 7 has its entrance end 340 in communication with channel 193 of system 100 of FIG. 1 and exit end 350 acts as an output channel 107.

The filter 305 in FIG. 7 is filled with dry air acting as a carrier gas. The dry air enters the filter 305 at entrance end 340. Entrance end 340 may be coupled to channel 193 shown in FIG. 1, such that the dry air may be pumped through the filter 305 by pump 170 in the manner shown in FIG. 1. The dry air then passes through the portion of the filter 305 located inside of chamber 111, wherein contaminants existing in sample substance 104 may permeate through the permeable membrane 306 of the filter 305 in a manner similar to that described above with respect to filters 205A-C. These contaminants (labeled "analytes" in FIG. 7) which permeate through the permeable membrane 306 then become intermingled with the dry air flowing through the filter 305 and are carried along with the dry air as it travels through remainder of the filter 305 towards exit end 350 located outside of chamber 111. The dry air and accumulated contaminants (or "analytes") are then expelled at exit end 350.

Because the extraction sampler 110 shown in FIG. 7 does not have an output channel, filter 305 also acts as output channel 107, ultimately expelling its contaminated dry air into moisture sensor 108 at exit end 350.

Referring back to FIG. 1, the carrier gas from output channel 107, regardless of which of the extraction samplers 110 of FIGS. 1, 2, and 7 is used, is transported to a moisture sensor 108. The moisture sensor 108 is coaxially mounted with the output channel 107, prior to the membrane desorber 112. The purpose of the moisture sensor 108 is to measure and detect $H_2O$ levels in the carrier gas expelled from the extraction sampler 110. This allows the ionization reaction chamber gate to properly produce the ions to be analyzed by the IMS spectrometer 120 and DMS spectrometer 130, wherein the carrier gas needs to remain largely free of moisture. If the moisture sensor indicates a high moisture value, the system is shut down, indicating that the extraction sampler 110 needs to be checked.

From the moisture sensor 108, the carrier gas together with any contaminants gathered from the extraction sampler 110, flow through a membrane desorber 112, wherein the analytes may concentrated by adsorption and desorption at a polymer surface which may be pulse heated, and into an APCI chamber 115.

The second flow control unit 192 also acts to deliver carrier gas into the APCI chamber 115. The second flow control unit 192, which sent some carrier gas through channel 193 into the extraction sampler 110 (previously discussed), simultaneously sends the remainder carrier gas through channel 194 and into the calibrant container 195. This flow of carrier gas, as with most carrier gas flows throughout the ion mobility sensor system 100, is driven at least in part by the flow controller 170.

The calibrant container 195 includes a calibrant chemical with well-known characteristic features like drift times in an IMS spectrometer and compensation voltages in a DMS spectrometer. The purpose of sending the carrier gas through the calibrant container 195 is to collect a sample of the calibrant chemical for use with the subsequent ion analysis. By including a calibrant chemical with well-known features, the IMS spectrometer 120 and the DMS spectrometer 130 can be calibrated through relative drift times and compensation voltages to accurately compute and determine which contaminants exist in sample substance 104. The carrier gas, coupled with a sample of the calibrant chemicals from the calibrant container 195, travel into the APCI chamber 115 through channel 199.

Figure 8:
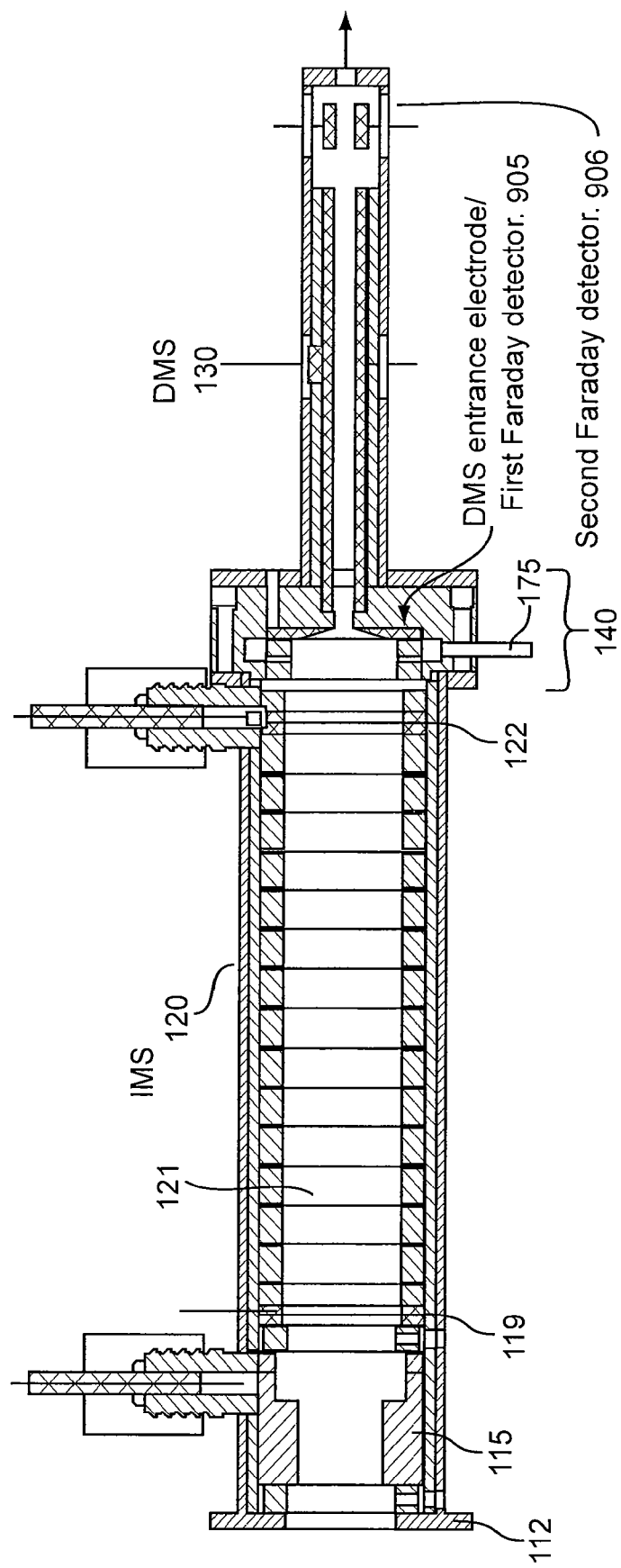
FIG. 8 shows a first cut-away view of a portion of the ion mobility sensor system shown in FIG. 1.
Figure 9:
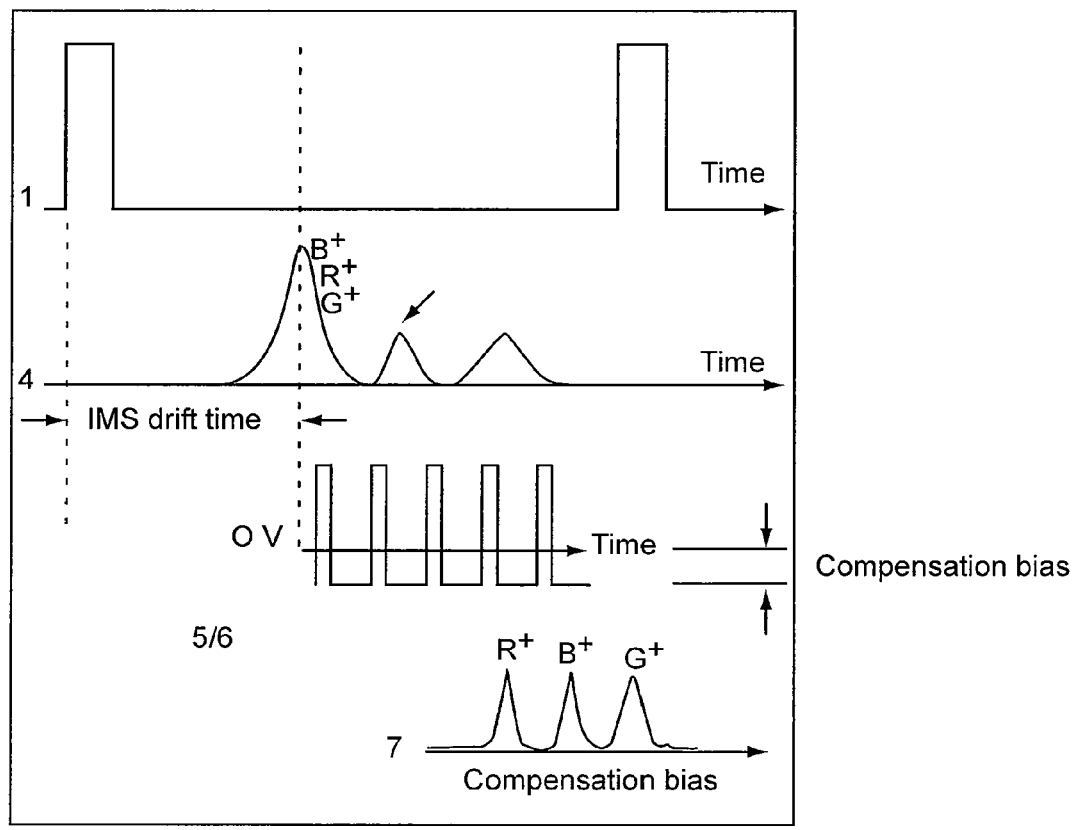
FIG. 9 illustrates possible time sequences of electric potentials applied to various electrodes, and signals from two Faraday detectors, as they are applied to the system shown in FIGS. 1 and 8.

Reference to FIG. 8 and FIG. 9 is beneficial for offering additional understanding of the functionality of the membrane desorber 112 and subsequent components of the ion mobility sensor system 100.

For example, FIG. 9 illustrates time sequences of electric potentials applied to various electrodes, and signals from two Faraday detectors, as they are applied to the system shown in FIGS. 1 and 8. Specifically, the numeric reference label 1 in FIG. 9 corresponds to a graph that shows an electric voltage applied to the first B-N gate 119 of the IMS spectrometer 120. Label 4 in FIG. 9 corresponds to a graph that shows IMS signal response in the first Faraday detector, which is the entrance electrode 905 of the DMS spectrometer 130. Labels 5 and 6 in FIG. 9 correspond to a graph that shows an asymmetric electric waveform applied between the filtration gap between side electrodes 1120 and 1130. Label 7 in FIG. 9 corresponds to a graph that shows a DMS signal response detected in the second Faraday detector 906. These sequences help to illustrate how ions created in the APCI chamber 115 have electric potentials applied thereto so as to navigate through the IMS spectrometer 120, the IMS/DMS interface 140, and the DMS spectrometer 130.

Referring to FIGS. 1 and 8, carrier gas from the moisture sensor 108 flows through the membrane desorber 112 and into the APCI chamber 115. During this process, the membrane desorber 112 releases chemicals, including chlorinated hydrocarbons such as PCE, TCE, dichloroethene, vinyl chloride, and other VOCs, which enter the APCI chamber 115 with the carrier gas from the moisture sensor 108. Additionally, the membrane desorber 112 also acts as a filter, blocking unwanted $H_2O$ clusters from entering the APCI chamber 115.

Inside the APCI chamber 115, the chemicals released by the membrane desorber 112 interact with the carrier gas, producing various ions. In one embodiment, electrons generated by a pulsed source, such as a radioactive 63Ni source, a 10.6-eV UV lamp, or a corona discharge source can be used for generating initial reactant ions from the carrier gas which has passed into the APCI chamber 115. In order for this to occur, the carrier gas is ideally dry air, including only a few (for example, less than one hundred) parts-per-million (ppm) of moisture. Preferably, the dry air consists of around, or less than, 10 ppm of moisture.

For dry air, two ions at ambient pressure have been identified as $O^-(H_2O)_n$ (n=1,3) and $H^+(H_2O)_m$ (m=2-4) for negative and positive ions, respectively. The collision of one of these reactant ions with a chlorinated hydrocarbon, found in contaminated groundwater for example, leads to formation of molecular and product ions that are desired for further analysis by the IMS spectrometer 120 and DMS spectrometer 130.

With specific reference to the negative ions mentioned above, chemical ionization reactions associated with the contaminant chlorinated hydrocarbon (M) may be $$\text{Air} + e^- \rightarrow O^-(H_2O)_n + R \tag{5}$$

$$O^-(H_2O)_n + M \rightarrow Cl^-(H_2O)_n + R \tag{6}$$

where R is the remainder species associated with a specific hydrocarbon. These reactions may take place in the APCI chamber 115.

It should be noted that detection of negative ions by the ion mobility sensor system 100 does not offer specificity for particular halocarbons, because dissociative ionization results in $Cl^-(H_2O)_n$ as the main product, which is insufficient to identify a difference between multiple molecules containing Cl. But because a focus of the present invention is on chlorinated hydrocarbon as a whole, detection of a negative ion offers a high sensitivity. Additionally, detection of negative ions may be very useful when the contaminant to be identified is something other than chlorinated hydrocarbons such as, for example, various explosives, chemical warfare agents, or toxic industrial compounds.

Referring back to chlorinated hydrocarbons, it is with the positive ions previously mentioned that chemical specificity can be offered. Reactant ions may be formed in dry air in the APCI chamber 115 by the following reactions:

$$N_2^+ + 2N_2 \rightarrow N_4^+ + N_2 \tag{7}$$

$$N_4^+ + H_2O \rightarrow H_2O^+ + 2N_2 \tag{8}$$

$$H_2O^+ + H_2O \rightarrow H_3O^+ + OH \tag{9}$$

$$H_3O^+ + H_2O + N_2 \rightarrow (H_2O)_{n+1}H^+ + N_2 \tag{10}$$

$$(H_2O)_nH^+ + H_2O + N_2 \rightarrow (H_2O)_{n+1}H^+ + N_2 \tag{11}$$

The formation of positive ions by the release of, for example, PCE and TCE, by the membrane desorber 112 at atmospheric pressure has been observed in corona discharge mass spectrometry. These ions are formed through exchange reactions, such as those shown below, with intermediate reagent ions like $NO^+(H_2O)_n$ or $H_2O^+$.

$$M + H_2O^+ \rightarrow M^+ + H_2O \tag{12}$$

$$M + NO^+(H_2O)_n \rightarrow M^+(H_2O)_n + NO \tag{13}$$

$$TCE^+ + H_2O \rightarrow C_2H_2CL_2O^+ + HCl \tag{14}$$

It is noted that the relative abundance of positive ions generated depends on conditions of concentration of $H_2O$, concentration of M, and other ionization and detection parameters. Significantly, all of these positive ions are associated with the composition of parent chlorinated hydrocarbons.

In an embodiment such as that described above, there is a high probability of formation of both positive and negative ions from chlorinated hydrocarbons. The APCI chamber 115 in this way is capable of producing ions which can be analyzed by the IMS spectrometer 120 and DMS spectrometer 130 for the purposes of contaminant data gathering and identification.

The ions produced by the APCI chamber 115 are injected into the IMS spectrometer 120 by the first B-N gate 119 of the IMS spectrometer 120. The operation of the first B-N gate 119 is well-known, and relies on the application of periodic pulses to allow charged particles to pass directly through the gate at certain time windows. This injection step starts the clock for drift time to be measured by the IMS spectrometer 120. The remaining waste molecules and compounds from the ion production in the APCI chamber 115 are not injected into the IMS spectrometer 120.

When the IMS spectrometer 120 is operating in positive mode, a constant electric field is generated inside the IMS spectrometer 120 such that positive ions travel through the drift channel 121 and towards the second B-N gate 122, while most negative ions which were formed are simply neutralized by the IMS electrodes. When the IMS spectrometer 120 is operating in negative mode, the constant electric field generated inside the IMS spectrometer 120 is configured such that negative ions travel through the IMS spectrometer 120 while positive ions are neutralized. This neutralization may be take place as a result of the ion charge's interaction with the constant electric field. Most neutralized or waste molecules and compounds which do not move down the drift channel 121 are sent into channel 118 to be ultimately flushed out by pump 170 through channel 155 and out of the ion mobility sensor system 100.

Those ions that successfully pass through the first B-N gate 119 are delivered into the drift channel 121 of the IMS spectrometer 120 for analysis. The ions passing through the second B-N gate 122 are sent to the IMS/DMS interface 140 and the DMS spectrometer 130 of ion mobility sensor system 100.

Once the ions are passed into the IMS spectrometer 120, the IMS spectrometer 120 performs IMS preliminary separation to begin identifying the specific contaminants from sample substance 104. IMS refers to a separation technique that is based on the linear relationship between ion drift velocity and an applied electric field. Generally in IMS, the ions drift in a gas cell, the drift channel 121, at ambient pressure and so can be used without the need to create a vacuum, which provides the considerable advantage of low power consumption. Ions in a reaction region are extracted and injected as ion swarms into a drift region wherein separations occur through differences in drift velocities ($V_d$) of the ion swarms in an electric field (E) of a few hundred V/cm. The drift velocities can be associated to molecular structure through the mobility coefficient K and linearly depend on the electric field E:

$$V_d = KE \qquad (9)$$

This separation by ion mobility creates selectivity for determination of chemical identity. In IMS, ions are characterized by a collision cross-section of ions with drift molecules, as opposed to a mass spectrometer where ions are characterized by a mass-to-charge ratio (m/Z).

The IMS spectrometer 120 performs linear IMS, which describes the linear relationship between the ion velocities and the constant electric field inside the IMS spectrometer 120. Inside the IMS spectrometer 120, the ions move with their characteristic velocities depending on their mobility and on the magnitude of the driving electric field. Since the field is common for all the ions, higher-mobility ions reach the second B-N gate 122, at earlier times, while lower-mobility ions arrive later. This mobility is shown by the graph labeled 4 in FIG. 9. A pulse, generated by electronics 125 for the IMS spectrometer 120 and used to initiate the first B-N gate 119, is used to drive the second B-N gate 122 with a tunable delay time generated by the electronics 125. This delay time is used to select desirable ions entering IMS/DMS interface 140. If the time of ions traveling between the first B-N gate 119 and the second B-N gate 122 is the same as the set delay, these ions may be able to enter the IMS/DMS interface 140. This delay time, which is recorded by the electronics 125, is later used, in conjunction with compensation voltages from the DMS spectrometer 130, to identify which contaminants exist in the liquid (groundwater) 104.

The mobilities for chlorinated hydrocarbons, which range from 2.4-2.7 $cm^2V^{-1}s^{-1}$, are usually higher than those for most other chemicals in groundwater, such as large VOCs, which have mobilities of less than $K_0$=2.3 $cm^2V^{-1}S^{-1}$. The IMS spectrometer 120 can be configured to isolate the group of chlorinated hydrocarbons from low- and high-mobility species, and thus is useful as the inlet for a secondary ion analysis performable by the DMS spectrometer 130. This separation can prevent many interferents from entering the region wherein secondary separation by the DMS spectrometer 130 occurs. In this way, the IMS spectrometer 120 can be used, as shown in FIGS. 1, 8, and 9, both to separate these ions from unknown chemicals obtained from field water and to serve as an inlet filter for the DMS spectrometer 130. Although with specific respect to chlorinated hydrocarbons, the IMS spectrometer 120 cannot separate each chlorinated hydrocarbon from the rest due to the limited resolution, it filters many other disparate groups of ions out of the sample gas to be inputted into the DMS spectrometer 130.

The ions of the chlorinated hydrocarbon ions can be guided to the entrance of the IMS/DMS interface 140 by selecting an IMS drift time window and applying proper static potentials in DMS spectrometer 130, as shown in FIG. 9.

The IMS spectrometer 120 can be controlled by the electronics 125, which applies and controls the electric field used in the IMS spectrometer 120. The electronics 125 may generate a constant electric field using an electrode system, or any other system capable of generating a constant electric field inside the IMS spectrometer 120. The electronics 125 includes drivers sampling pump, carry gas pump, ion injection pulse, drift field, asymmetric RF bias, amplifiers, and display. The electronics 125 may include a processor and/or memory for recording drift times and other data associated with the ions, or for conducting analysis of the data recorded. The electronics 125 may also include a display to view any data, computations, or other information contained by any computer readable medium with other components in the electronics 125.

As previously stated, the IMS spectrometer 120 may be operated in positive mode or negative mode. In positive mode, positive ions are moved by the constant electric field from the first B-N gate 119 to the second B-N gate 122, while the negative ions are neutralized. This is true regardless of what contaminants are being analyzed. In negative mode, as previously stated, the opposite takes place, with the negative ions moving through the IMS spectrometer 120 and the positive ions being neutralized.

While when analyzing a sample substance 104 for chlorinated hydrocarbons it may be desirable to operate the ion mobility sensor system 100 in positive mode to provide specificity in what contaminants might be present, it may also be desirable to operate the ion mobility sensor system 100 in negative mode under the same conditions to provide additional information regarding the quantity of contaminants in a sample substance 104. Doing so may provide many benefits, including the reduction of false positive or false negative results. Additionally, alternating between positive and negative mode at set intervals may also be beneficial as a way of gathering more detailed information about the sample substance 104.

Figure 10:
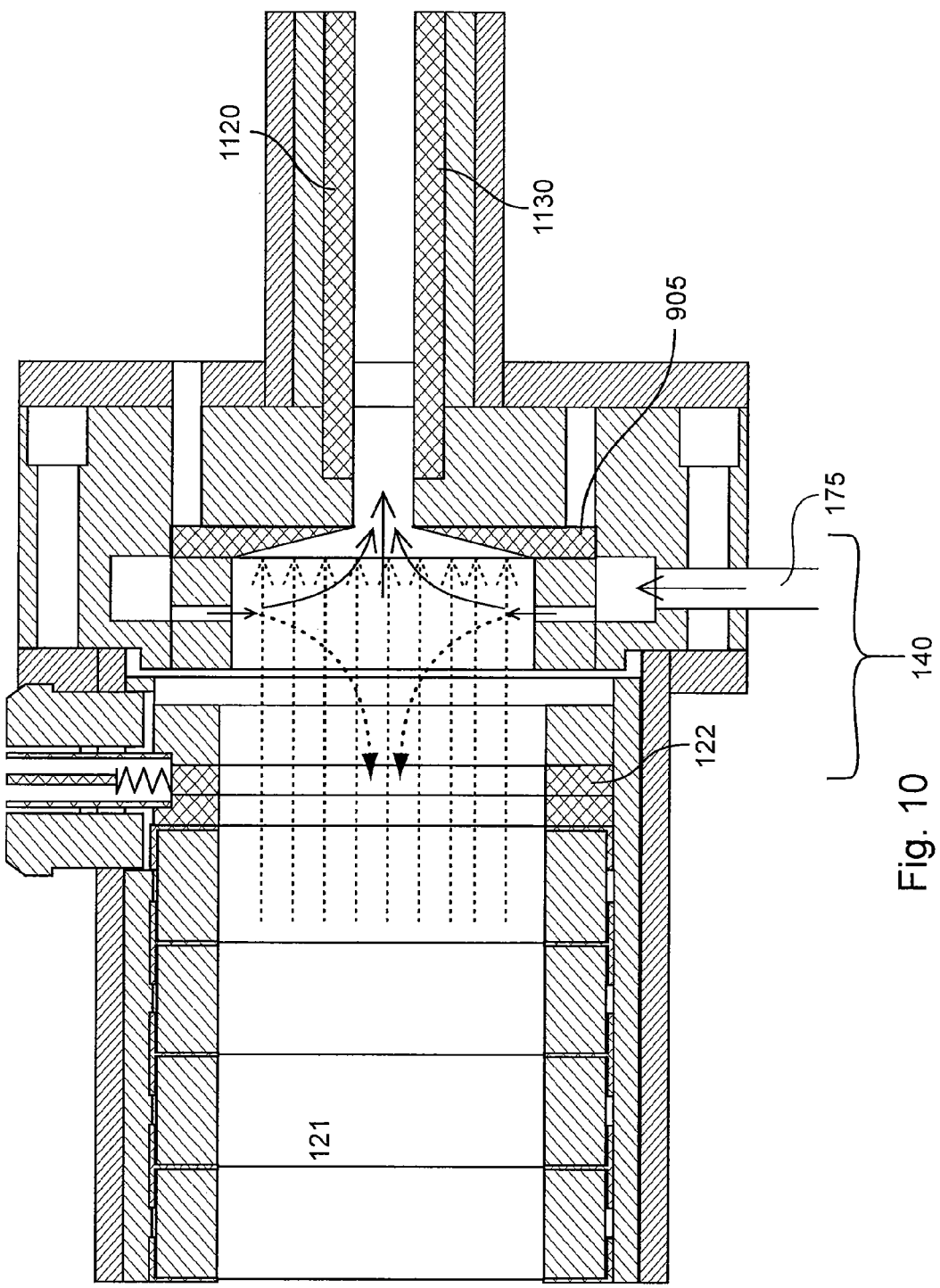
FIG. 10 shows a close-up view of a cut-away view of an embodiment of the IMS/DMS interface to be used with the ion mobility sensor system of FIGS. 1 and 8 in accordance with the present invention.

The ions of the chlorinated hydrocarbons can be guided to the entrance of the IMS/DMS interface 140 by selecting an IMS drift time window. Reference to FIG. 10, which shows a close-up view of cut-away view of an embodiment of the IMS/DMS interface of the ion mobility sensor system 100 of FIG. 1, proves helpful in describing the IMS/DMS interface 140.

Ions pushed through the IMS spectrometer 120 pass through a second B-N gate 122 (see FIG. 10), which may define the entrance to the IMS/DMS interface 140. A portion of the carrier gas from the first flow control 190 may flow through channel 175 into the IMS/DMS interface 140 as shown in FIGS. 1 and 10. Alternatively, channel 175 may be attached to the IMS spectrometer just before the IMS/DMS interface 140. This flow is driven by the pump 170, and facilitates the use of both the IMS spectrometer 120 and the DMS spectrometer 130.

A first portion of the carrier gas, which is preferably dry air, flowing into the IMS/DMS interface 140 at channel 175 flows through the IMS spectrometer 120 in a direction opposite that of the flow of ions previously discussed. This flow of gas is very useful in the operation of the IMS spectrometer 120, in that it aids in preventing the contamination of samples of ions in the drift channel from entering the IMS/DMS interface 140. Neutralized ions, neutral contaminants, and those ions with a polarity opposite to that of the ions intended to be propagated through drift channel 121 are pushed by the flowing gas back toward the first B-N gate 119 and ultimately flushed from the system via channel 118. The air does not, however, prevent most of those ions propelled by the constant electric field generated by the electronics 125 for the IMS spectrometer 120 from traveling down the drift channel 121 towards the second B-N gate 122. This may be particularly true where the force on the traveling ions due to the electric field is many times greater than any force generated by the flow of the carrier gas.

A second portion of the carrier gas from channel 175 flows through the DMS spectrometer 130 in a direction which is the same as that of the general flow of ions through the DMS spectrometer 130, and in this manner, aids in driving the flow of ions from one end of the filtration gap to the other end. In the DMS spectrometer 130, as will be discussed below, the electric field which the ions are subjected to may not propel or aid in propagating the ions down the DMS spectrometer 130. Instead, this propagation between the DMS entrance electrode 905 and the DMS exit electrode 906 is aided by the flow of carrier gas through the DMS spectrometer 130.

In one embodiment, the flow rate of carrier gas through channel 175 may be between 100 standard cubic centimeters per minute (sccm) and 2000 sccm. This flow rate may depend on the opening to the DMS spectrometer 130. The flow rate per unit area for the DMS spectrometer 130 may be much larger than that for the IMS spectrometer, with the flow rate in one embodiment in the DMS spectrometer 130 being ten times larger than the flow rate in the IMS spectrometer 120. This may be due to the fact that the opening and channel of the DMS spectrometer 130 is much smaller than the drift channel 121 of the IMS spectrometer 120. In this way, the channel 175 may be useful for aiding the operation of both the IMS spectrometer 120 and the DMS spectrometer 130.

In one embodiment, while both the first flow control 190 and the second flow control 192 separate the flow of carrier gases, the pump 170 acts to propagate the movement of the carrier gas. The system may include one flow controller or pump 170 as shown in FIG. 1, or may alternatively include a plurality of flow controllers and/or pumps placed throughout the system.

As previously noted, the IMS/DMS interface 140 may be defined as the space between the second B-N gate 122 and the DMS entrance electrode 905. The ion driver for the IMS spectrometer 120 is the constant electric field, while the ion driver for the DMS spectrometer 130 is the flowing carrier gas from channel 175. The IMS/DMS interface 140 may be configured so that these ion drivers overlap with each other, allowing spatial overlap between the electric field generated by the electronics 125 for the IMS spectrometer 120, and the DMS carrier gas flow, which includes a portion of the flow of carrier gas from channel 175.

In this IMS/DMS interface 140, an electric field generated by the difference of potentials between the second B-N gate 122 and the DMS entrance electrode 905 may exist. This potential difference aid in propagating desired ions from the exit of the IMS spectrometer 120 into the entrance of the DMS spectrometer 130. The potential difference across the IMS/DMS interface 140 may partially overlap with the flow of carrier gas into the DMS spectrometer 130, as well as with the flow of ions exiting the IMS spectrometer 120. Because of these overlaps, ion interactions involve diffusive forces due to ion-gas collisions, flow dynamics, and electric force.

For the overlap of the potential difference in the IMS/DMS interface 140 with the flow of ions exiting the IMS spectrometer 120 near the second B-N gate 122, electric force dominates the ion driving because the flow rate per area for any carrier gas is small. This overlap is the same as that in the drift channel 121 of the IMS spectrometer 120. The potential difference existing across the IMS/DMS interface 140 implements a force on the travelling ions in the same general direction as the force on the ions generated by the electronics 125 for the IMS spectrometer 120 in the drift channel 121. As such, the ions may continue on their movement towards the DMS entrance electrode 905 in a steady manner. The flow rate may be small, as previously mentioned, because the general cross-sectional area of the IMS spectrometer 120 may be considerably larger than that of the DMS spectrometer 130.

The average direction of this flow of carrier gas from channel 175 into the IMS/DMS interface 140 is converged to the DMS entrance electrode 905. This flow pattern generates an overlap with the interfacial electric field described above. This overlap exchanges the driving forces of ion movement from electric field, which is used by IMS, to flow, which is used in DMS. Then this overlap prevents ion loss in the interface, as many ions may not be able to pass through the IMS/DMS interface 140 and into the DMS spectrometer 130 with the aid of the potential difference between the second B-N gate 122 and the entrance electrode 905 alone.

However, for the portion of overlap of the electric field between the second B-N gate 122 and the entrance electrode 905 with the flow of the carrier gas near the DMS spectrometer 130, the flow of carrier gas becomes a larger factor in driving the ion movement because the flow rate per area is much higher, and also because there is no electric field being generated within the DMS spectrometer 130 which would otherwise force ions to be travelling in the same general direction (the electric field in the DMS spectrometer 130 pulls ions back and forth between the two side electrodes 1120 and 1130, not between the DMS entrance electrode 905 and the DMS exit electrode 906). Because the flow rate of the carrier gas increases as one nears the DMS entrance electrode 905, the overlap between the potential difference in the IMS/DMS interface and the DMS carrier gas flow prevents ion loss in the interface region.

In positive mode the electric potential at the first B-N gate 119 is larger than the electric potential at the second B-N gate 122, which in turn is larger than the electric potential at the DMS entrance electrode 905. In one embodiment, the electric potentials at each of those points are positive. The reverse situation may exist when the ion mobility sensor system 100 is operating in negative mode, where the electric potential at the first B-N gate 119 is less than the potential at the second B-N gate 122, which in turn is smaller than the electric potential at the DMS entrance electrode 905. In some embodiments, the potentials at each of these three points are all negative. In either positive or negative mode, the potential of the DMS entrance electrode 905 is generally zero, but can be other values, typically between −100 volts and 100 volts. In one embodiment, the electric field in the interface is 300 V/cm and the gas flow rate is 0.3-2 L/min. When operating in positive mode, then, the potential difference drives positive ions to pass through the IMS/DMS interface 140 into the DMS spectrometer 130, while repelling negative ions. In negative mode, the potential difference drives negative ions through the IMS/DMS interface 140 into the DMS spectrometer 130, while repelling positive ions.

The IMS/DMS interface 140 is configured to enable the transfer of ions from the IMS spectrometer 120, which is usually cylindrical, to the DMS spectrometer 130, which is usually planar, without ion loss. This may mean that the IMS/DMS interface 140 has one cylindrical open space matching the dimensions of the IMS spectrometer 130 drift channel exit, while the other end may be rectangular shape to match the dimensions of the DMS spectrometer 130 entrance end. In one embodiment, the internal surface of the IMS/DMS interface 140 may be smooth to facilitate the passage of an optimal number of ions. The length of the IMS/DMS interface 140 may be any distance. In a preferred embodiment, the length of the IMS/DMS interface 140 is between 0.3 cm and 10 cm.

A first component that transmits, passes, allows to flow through, or otherwise sends a gas, fluid, or other substance to a second component (directly or indirectly through one or more other components) may be considered or referred to as "upstream" from or relative to the second component. The second component which receives or accepts some or all of the gas, fluid, or other substance from the first component (directly or indirectly through one or more other components) may be considered or referred to as "downstream" from or relative to the first component.

In some embodiments, the IMS spectrometer 120 may be positioned upstream from the IMS/DMS interface 140 and/or DMS spectrometer 130. "Upstream" in this context may refer to a configuration of the IMS spectrometer and IMS/DMS interface 140 where ions flow through the IMS spectrometer 120 toward and into the IMS/DMS interface 140. The DMS spectrometer 130 may be positioned downstream from the IMS spectrometer 120 and/or IMS/DMS interface 140. "Downstream" in this context may refer to a configuration of the DMS spectrometer 130 and IMS/DMS interface 140 where ions flow from the IMS/DMS interface 140 into and through the DMS spectrometer 130 away from the IMS/DMS interface 140. The terms "upstream" and "downstream" may be positional terms which refer to the position of one component relative to another component. In some systems, components referred to as "upstream" or "downstream" relative to one another may or may not include or have a flow or stream of anything commonly flowing between them. For example, an IMS spectrometer 120 may be referred to as being upstream relative to a DMS spectrometer 130 as defined by a flow of fluid through the DMS spectrometer 130, even if the fluid does not also actually flow through the IMS spectrometer 120.

As an example, in FIG. 1, ions may flow from the first B-N gate 119, left to right through the IMS spectrometer 120, through the IMS/DMS interface 140, and left to right through the DMS spectrometer 130. In FIG. 1, the arrow in the IMS/DMS interface 140 pointing towards the DMS spectrometer 130 may show a flow of a portion of the fluid from the first flow control unit 190 flowing with the flow of ions into and through the DMS spectrometer 130. In this example, as defined by the flow of ions and the arrow in the IMS/DMS interface 140 pointing towards the DMS spectrometer 130, the IMS spectrometer 120 may be positioned upstream relative to the IMS/DMS interface 140 and/or DMS spectrometer 130, and the DMS spectrometer 130 may be positioned downstream relative to the IMS spectrometer 120 and/or IMS/DMS interface 140. In FIG. 1, the arrow in the IMS spectrometer 120 (pointed in the opposite direction as the arrow in the IMS/DMS interface 140) may show a flow of a portion of fluid from first flow control unit 190 flowing against the flow of ions in the IMS spectrometer 120.

Figure 11:
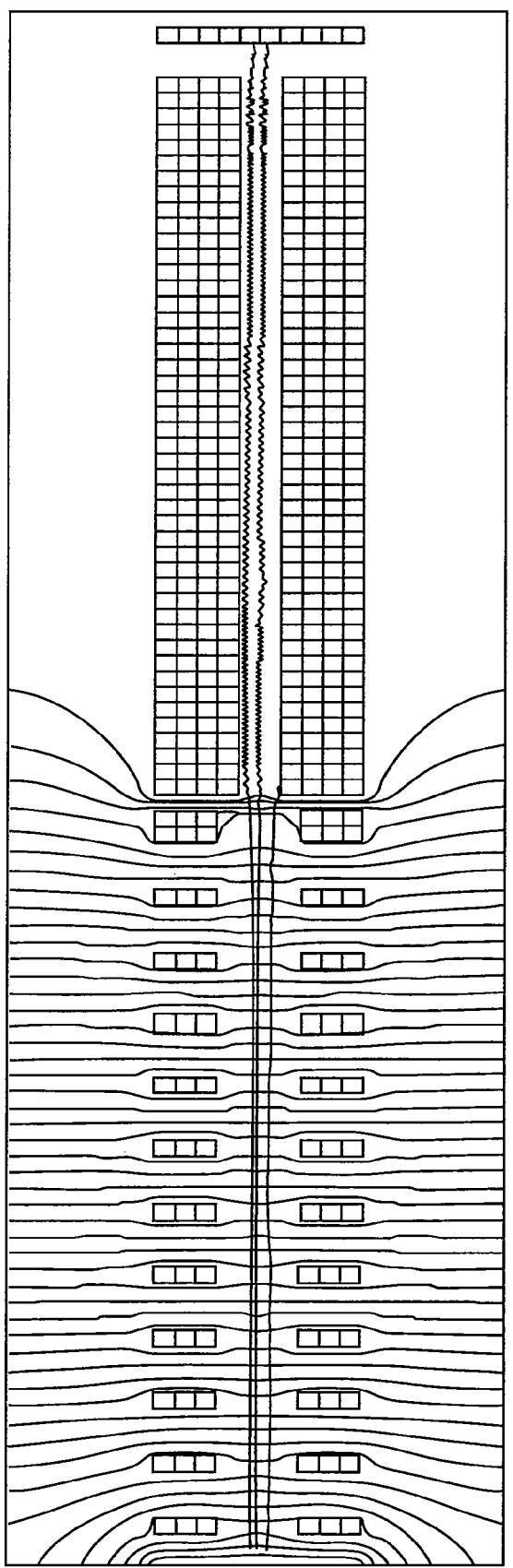
FIG. 11 shows a simulation of ion trajectories at the junction of an embodiment of an IMS and DMS interface on the ion mobility sensor system of FIG. 1.

FIG. 11 shows a Monte Carlo simulation of ion trajectories at the junction of an IMS/DMS interface 140 on the ion mobility sensor system 100 of FIG. 1. This simulation regards an interface length of 0.3 cm, an electric field of 300 V/m, and a gas flow rate of 2 L/m. This simulation shows two out of three ions successfully passing all the way through the IMS spectrometer 120, the IMS/DMS interface 140, and the DMS spectrometer 130.

Returning now to the FIGS. 1 and 8, those ions successfully passing through the IMS/DMS interface 140 enter the DMS spectrometer 130 for a second dimensional analysis.

In general, the DMS spectrometer 130 operates differently than the IMS spectrometer 120. For ion transport in ambient atmosphere under an electric field (higher than 500 V/cm), ion drift velocities vary with the field non-linearly. The DMS spectrometer 130 operates to take advantage of this non-linear relationship. The ultimate purpose of the DMS spectrometer 130 is to achieve chemical specificity of chlorinated hydrocarbons after these chlorinated hydrocarbons have been separated from other compounds by the IMS spectrometer 120.

Figure 12:
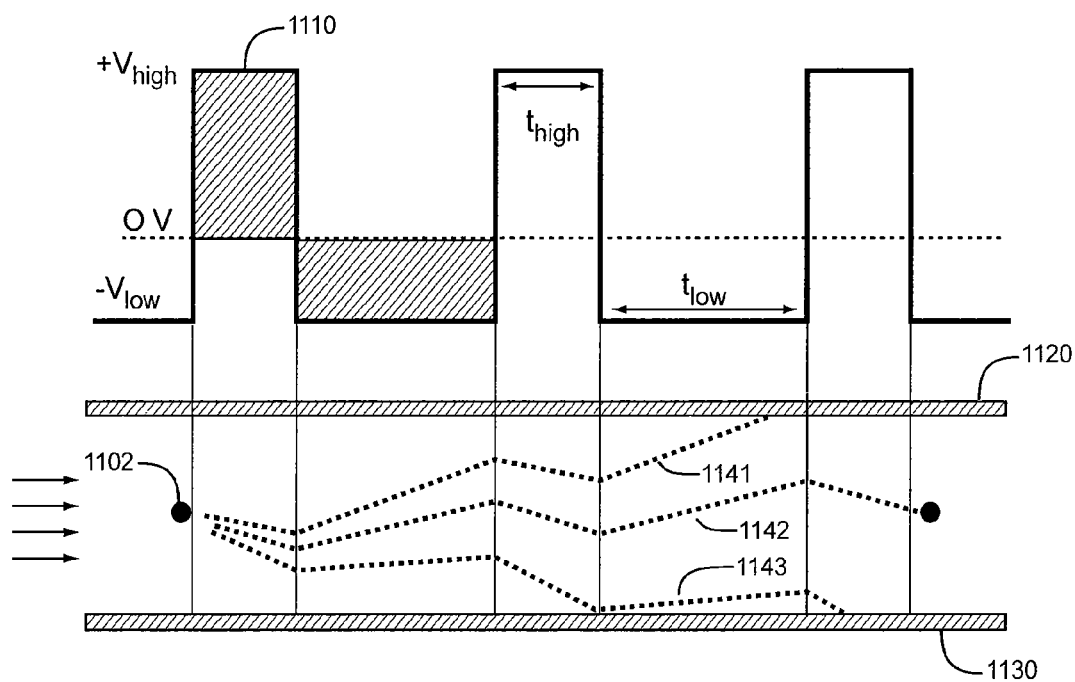
FIG. 12 shows possible asymmetric waveforms applied to the gap in an embodiment of a DMS to be used with the ion mobility sensor system of FIG. 1, and the ion trajectories in the drift gap resulting from the asymmetrical waveform.

DMS spectrometer 130 functions in a manner depicted in FIG. 12. FIG. 12 shows an ion 1102 between two side electrodes 1120 and 1130. The ion 1102 is pushed by the carrier gas flowing from channel 175 in the x-direction. FIG. 12 shows one possible asymmetric waveform, a square periodic pulse, applied to the gap in the DMS spectrometer 130 to be used with the ion mobility sensor system 100 of FIG. 1, as well three different ion trajectories 1141-1143 for ion 1102 in the drift gap resulting from the asymmetrical waveform. This waveform may be applied by the electronics 135 for the DMS spectrometer 130. The electronics 135 may alternatively gen erate an asymmetric waveform, such as a bisinusoidal waveform:

$$\frac{V_{max}}{3}[2\sin(wt) + \sin(2wt - \pi/2)],$$

where $V_{max}$ is the peak voltage of the RF waveform, varying from 500 volts to 5000 volts depending on the gap dimension. Additionally or alternatively, any number of asymmetric waveforms may be applied by the electronics 135 for the DMS spectrometer 130.

The DMS spectrometer 130 operates to separate each of the chlorinated hydrocarbon ions. Referring to FIG. 12, ions, like ion 1102, are carried with a flow of gas through a narrow gap between two side electrodes 1120 and 1130 towards a detector. The high frequency, high voltage asymmetric waveform 1110 applied between the electrodes 1120 and 1130 results in an electric field that causes ions, like ion 1102, to undergo fast oscillations perpendicular to the gas flow (the gas flow is represented by horizontal arrows to left of entrance of side electrodes 1120 and 1130). The ions consequently experience a slow net displacement toward the detector based upon differences in mobility coefficients during the oscillations. Ion trajectories 1141, 1142, and 1143 of three kinds of ions with various mobility coefficients in a high field are shown in FIG. 12. Only the ions with a total transverse displacement having a value less than the width of the distance between the side electrodes 1120 and 1130 will pass through the DMS spectrometer 130. An ion that can reach the detector through the gap between side electrodes 1120 and 1130 correlates to a characteristic compensation voltage.

Separation ability in the DMS spectrometer 130 depends on differences in ion mobility at low and high electric fields. Ion drift velocity from the DMS entrance electrode 905 to the exit electrode 906 in the DMS spectrometer 130 is understood to vary non-linearly for high electric field (E/N=100 Townsends, where E is the electric field and N is the density of neutral drift molecules):

$$V_d = K_0(1 + \alpha(E/N)) \quad (10)$$

where $\alpha(E/N) = \alpha_1(E/N)^2 + \alpha_2(E/N)^4 + \alpha_3(E/N)^6 + \ldots$.

In order to accomplish this separation of chlorinated hydrocarbons that cannot be done by IMS spectrometer 120, the α coefficient for each of the chlorinated hydrocarbons needs to be different in the high field region. In one embodiment, the DMS spectrometer 130 is operated at 100 E/N without consuming large amounts of power. Under such circumstance, α of the product ions of 1,2-dichloroethane, 1,1, 2-trichloroethane, and 1,1,1,2-tetrachloroethane may show the desired large deviation from each other. This deviation may result in separation of the compensation voltages.

The DMS spectrometer 130 is controlled by the electronics 135, which applies and controls the electric field used in the DMS spectrometer 130. The electronics 135 may include drivers sampling pump, carry gas pump, ion injection pulse, drift field, asymmetric RF bias, amplifiers, and display. The electronics 135 may include a processor and/or memory for recording compensation voltages and other data associated with the ions, or for conducting analysis of the data recorded. The electronics 135 may also include a display to view any data, computations, or other information contained by any computer readable medium with other components in the electronics 135. Additionally the electronics 135 is capable of recording and plotting drift times and compensation voltages, as well as determining the type and level of contaminants or other molecules present in the fluid to be tested (in the embodiment of FIG. 1, this is sample substance 104).

Figure 13:
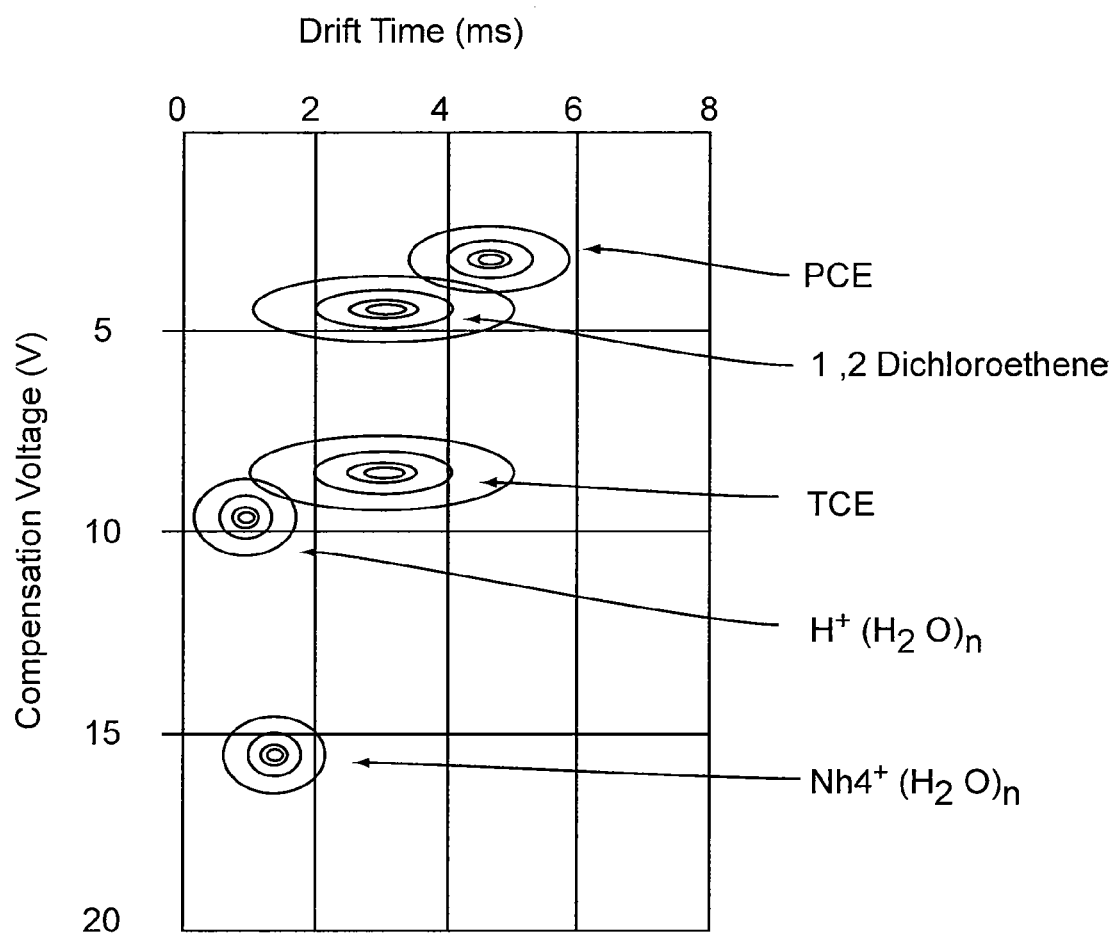
FIG. 13 shows a two-dimensional spectrum for a number of chemicals, illustrating drive time versus compensation voltage for these chemicals.

Because the IMS drift-time and DMS compensation-voltage are both recorded, a two dimensional spectrum illustrative of characteristics for certain water contaminants can be created. FIG. 13 shows such a two-dimensional spectrum for a number of chemicals, illustrating drive time versus compensation voltage for these chemicals. IMS drift times in FIG. 13 are based on gas chromatography ("GC")-IMS data of chloroethenes, while DMS compensation voltages are based on GC-DMS data of chloroethane chemicals.

The spectrum in FIG. 13 shows that it is difficult to separate 1, 2 dichloroethene from TCE by drift time measurements alone. Similarly, it is difficult to distinguish TCE from $H^+(H_2O)_n$ ions purely through the use of compensation voltage measurements. However, by comparing the plot of drift times and compensation voltages for the ions passing through the IMS spectrometer 120 and the DMS spectrometer 130 to the spectrum in FIG. 13, one can quickly, easily, and inexpensively determine what contaminants exist in the sample substance 104 being analyzed.

In one embodiment, spectra of analytes in the carrier gas are displayed on the on-site ion mobility sensor system 100 by a display or alerting device coupled to the control and signal unit 150 and a battery and driver unit 160 of the ion mobility sensor system 100. Alternatively or in addition, these spectra of analytes can be transmitted via a wireless or wired communication to any off-site location. Additionally or alternatively, these spectra may be stored in any medium capable of storing such data, including paper graphs or charts, or any computer readable medium for later review. In these ways, the ion mobility sensor system 100 may operate completely without human attendance or supervision.

Referring now back to FIG. 1, ions which have passed through the DMS spectrometer 130 are expelled through opening 132 into channel 118. From here, like the waste molecules, compounds, and ions in the APCI chamber 115, the ions passing through the DMS spectrometer 130 are pumped by pump 170 through channel 155 and out of the ion mobility sensor system 100.

The construction of the combination IMS spectrometer 120 and DMS spectrometer 130 in one embodiment may be less than 14 cm long. Alternatively, these components could be constructed on a larger or smaller scale as desired.

Ion mobility sensor system 100 as shown in FIG. 1 is configured to analyze groundwater for contaminants. However, the system is not limited to the analysis of groundwater, but instead may be used to analyze any fluid capable of being analyzed by both a IMS spectrometer and a DMS spectrometer. Additionally, the ion mobility sensor system 100 is not limited to the analysis of contaminants, but instead may be used to analyze or detect any specified molecule capable of being identified in some manner (in whole, in part, or perhaps only as a member of a larger group capable of being identified) by the combination of a IMS spectrometer and a DMS spectrometer.

Use of the ion mobility sensor system 100 may, for example, be used to identify explosive molecules, such as TNT, RDX, and HMS, which have high electron affinities. This feature allows preferential formation of explosive-related negative ions in the APCI 115, leading to sensitive detection. This is why many IMS detectors are used in airport security check points. However, the false alarm rate of IMS detectors is high. The present ion mobility sensor system 100, which provides the combination IMS spectrometer 120 and DMS spectrometer 130, is useful particularly in negative mode, for reducing both false positive and false negative rates, because two-dimensional separation is be enabled. Alternatively, most species of chemical warfare agents (CWA), toxic industrial compounds (TICS), and illegal drugs have high proton affinities, indicating efficient formation of positive ions. The present ion mobility sensor system 100, including both the extraction sampler 110 and the combination of the IMS spectrometer 120 and DMS spectrometer 130, can be used for reliable detection of these threat agents, particularly when the system 100 is operated in positive mode.

When using the ion mobility sensor system 100 to detect any contaminant or other analyte, the system 100 may be used in either positive or negative mode as desired. Additionally or alternatively, the extraction sampler 110 may be used as described. In some embodiments, while the IMS/DMS interface 140 is configured as described above, a different extraction sampler may be used to first gather the contaminants or analytes for analysis.

While the invention has been described above by reference to various embodiments, it will be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. An ion mobility sensor system comprising:
an ion mobility spectrometer comprising:
a first chamber having a first end and a second end extending along a first direction;
a first electrode system that generates a constant electric field parallel to said first direction;
a differential mobility spectrometer coupled to said ion mobility spectrometer comprising:
a second chamber having a third end and a fourth end configured such that a fluid may flow in a second direction from said third end to said fourth end;
a second electrode system that generates an asymmetric electric field within an interior of said second chamber;
wherein said ion mobility spectrometer and said differential mobility spectrometer form an interface region; and
wherein as defined by the flow of said fluid, said ion mobility spectrometer is positioned upstream relative to said interface region, and said differential mobility spectrometer is positioned downstream relative to said interface region;
wherein said first end and said third end are positioned facing one another so that said constant electric field enters said third end and overlaps said fluid flowing in said second direction.

2. The ion mobility sensor system of claim 1, wherein said first direction is aligned with said second direction.

3. The ion mobility sensor system of claim 1, wherein said first end is spaced from said third end.

4. The ion mobility sensor system of claim 1, wherein said interface region is configured such that a fluid exiting said ion mobility spectrometer system moves through said interface region and into said differential mobility spectrometer.

5. The ion mobility sensor system of claim 1, further including a contaminated substance to be analyzed by said ion mobility spectrometer, wherein said contaminated substance comprises a contaminant selected from the group consisting of chlorinated hydrocarbons, perchlorate, explosives, volatile organic compounds, chemical warfare agents, and toxic industrial compounds.

6. An extraction sampler, comprising:
a chamber comprising:
an inlet port for receiving a contaminated substance and directing said received contaminated substance to an interior portion of said chamber; and
an outlet port in communication with said interior portion and a substance conduit exterior to said chamber;
a first filter comprising:
a first channel that extends into said interior portion and has a first end and a second end that extend out of said interior portion, wherein said first channel contains a first fluid and said first channel is permeable to the extent that a first contaminant present in said contaminated substance is conveyed through a first wall defining said first channel and into said first fluid; and
a second filter comprising:
a second channel that extends into said interior portion and has a third end and a fourth end that extend out of said interior portion, wherein said second channel contains a second fluid and said second channel is permeable to the extent that a second contaminant present in said contaminated substance is conveyed through a second wall defining said second channel and into said second fluid.

7. The extraction sampler of claim 6, wherein said first channel is helical in shape.

8. The extraction sampler of claim 7, wherein said second channel is helical in shape.

9. The extraction sampler of claim 6, wherein said first fluid is a gas.

10. The extraction sampler of claim 7, wherein said second fluid is a gas.

11. The extraction sampler of claim 6, further comprising a third channel that extends into said interior portion and has a fifth end and a sixth end that extend out of said interior portion, wherein said third channel contains a third fluid and said third channel is permeable to the extent that a third contaminant present in said contaminated substance is conveyed through a third wall defining said third channel and into said third fluid.

12. The extraction sampler of claim 6, wherein said first contaminant is selected from the group consisting of chlorinated hydrocarbons, perchlorate, explosives, volatile organic compounds, chemical warfare agents, and toxic industrial compounds.

13. An ion mobility sensor system, comprising:
a first chamber having a first port to receive a fluid exterior of said chamber and a second port to have said fluid leave an interior of said first chamber;
an electrode system that generates an electric field within said interior of said first chamber;
an extraction sampler, comprising:
a second chamber comprising:
an inlet port for receiving a contaminated substance and directing said received contaminated substance to an interior portion of said second chamber; and
an outlet port in communication with said interior portion and a substance conduit exterior to said second chamber;
a filter comprising:
a channel that extends into said interior portion and has a first end and a second end that extend out of said interior portion, wherein said channel contains said fluid and said channel is permeable to the extent that a contaminant present in said contaminated substance is conveyed through a wall defining said channel and into said fluid.

14. The ion mobility sensor system of claim 13, further comprising:
a second filter comprising:
a second channel that extends into said interior portion and has a third end and a fourth end that extend out of said interior portion, wherein said second channel contains a second fluid and said second channel is permeable to the extent that a second contaminant present in said contaminated substance is conveyed through a second wall defining said second channel and into said second fluid.

15. The ion mobility sensor system of claim 13, wherein the electrode system generates a constant electric field.

16. The ion mobility sensor system of claim 13, wherein the electrode system generates an asymmetric electric field.

17. The ion mobility sensor system of claim 13, wherein said contaminated substance comprises a contaminant selected from the group consisting of chlorinated hydrocarbons, perchlorate, explosives, volatile organic compounds, chemical warfare agents, and toxic industrial compounds.

18. An ion mobility sensor system, comprising:
an ion mobility spectrometer that generates a constant electric field in a first direction along the length of the ion mobility spectrometer;
a differential mobility spectrometer coupled to said ion mobility spectrometer at an interface region; and
a flow operative device coupled to said interface region and configured to allow a fluid to be inserted into said interface region, wherein said fluid is divided into a first portion of fluid which flows in a second direction parallel to said first direction and acts as an ion driver for said differential mobility spectrometer, and a second portion of said fluid which flows through said ion mobility spectrometer in a third direction opposite said second direction; and
wherein as defined by the flow of said first portion of fluid, said ion mobility spectrometer is positioned upstream relative to said interface region, and said differential mobility spectrometer is positioned downstream relative to said interface region.

19. The ion mobility sensor system of claim 18, wherein said second portion of said fluid prevents neutral compounds within said ion mobility spectrometer from passing into said interface region.

20. The ion mobility sensor system of claim 18, wherein said ion mobility spectrometer is further configured to analyze a contaminated substance comprising a contaminant selected from the group consisting of chlorinated hydrocarbons, perchlorate, explosives, volatile organic compounds, chemical warfare agents, and toxic industrial compounds.

21. The ion mobility sensor system of claim 18, wherein said fluid acts as an ion driver for said differential mobility spectrometer by pushing ions through the differential mobility spectrometer in the third direction, the third direction being the same as the first direction.

22. The ion mobility spectrometer system of claim 1, wherein ions flow through said ion mobility spectrometer from said second end of said first chamber to said first end of said first chamber;
wherein said ions flow from said first end of said first chamber of said ion mobility spectrometer to said third end of said second chamber of said differential mobility spectrometer; and
wherein said ions flow through said differential mobility spectrometer from said third end of said second chamber to said fourth end of said second chamber.

23. The ion mobility sensor system of claim 18, wherein ions flow in said first direction through said ion mobility spectrometer; and
wherein said ions flow from said ion mobility spectrometer through said interface region and said differential mobility spectrometer.

* * * * *